US012624036B2

(12) United States Patent
Mates et al.

(10) Patent No.: US 12,624,036 B2
(45) **Date of Patent: *May 12, 2026**

(54) METHOD OF TREATING POST-TRAUMATIC STRESS DISORDER

(71) Applicant: INTRA-CELLULAR THERAPIES, INC., New York, NY (US)

(72) Inventors: Sharon Mates, New York, NY (US); Robert Davis, San Diego, CA (US); Kimberly Vanover, New York, NY (US)

(73) Assignee: INTRA-CELLULAR THERAPIES, INC., Bedminster, NJ (US)

(*) Notice: Subject to any disclaimer, the term of this patent is extended or adjusted under 35 U.S.C. 154(b) by 824 days.

This patent is subject to a terminal disclaimer.

(21) Appl. No.: 16/926,551

(22) Filed: Jul. 10, 2020

(65) Prior Publication Data

US 2020/0407362 A1 Dec. 31, 2020

Related U.S. Application Data

(63) Continuation of application No. 14/394,469, filed as application No. PCT/US2013/036512 on Apr. 14, 2013, now Pat. No. 11,053,245.

(60) Provisional application No. 61/624,291, filed on Apr. 14, 2012, provisional application No. 61/624,292, filed on Apr. 14, 2012, provisional application No. 61/624,293, filed on Apr. 14, 2012, provisional application No. 61/671,713, filed on Jul. 14, 2012, provisional application No. 61/671,723, filed on Jul. 14, 2012.

(51) Int. Cl.

| | |
|---|---|
| ***A61K 31/445*** | (2006.01) |
| ***A61K 31/4985*** | (2006.01) |
| ***A61K 31/5383*** | (2006.01) |
| ***A61K 45/06*** | (2006.01) |
| ***A61P 25/28*** | (2006.01) |
| ***C07D 471/14*** | (2006.01) |
| ***C07D 471/16*** | (2006.01) |

(52) U.S. Cl.

CPC .......... *C07D 471/14* (2013.01); *A61K 31/445* (2013.01); *A61K 31/4985* (2013.01); *A61K 31/5383* (2013.01); *A61K 45/06* (2013.01); *A61P 25/28* (2018.01); *C07D 471/16* (2013.01)

(58) Field of Classification Search

CPC .................................................. A61K 31/445

See application file for complete search history.

(56) References Cited

U.S. PATENT DOCUMENTS

| | | | |
|---|---|---|---|
| 2,490,813 | A | 12/1949 | Hughes et al. |
| 3,299,078 | A | 1/1967 | Pachter et al. |
| 3,813,392 | A | 5/1974 | Sellsdet et al. |
| 3,914,421 | A | 10/1975 | Rajagopala |
| 4,001,263 | A | 1/1977 | Plattner et al. |
| 4,115,577 | A | 9/1978 | Rajagopala |
| 4,183,936 | A | 1/1980 | Rajagopala |
| 4,219,550 | A | 8/1980 | Rajagopala |
| 4,238,607 | A | 12/1980 | Rajagopala |
| 4,389,330 | A | 6/1983 | Tice et al. |
| 4,522,944 | A | 6/1985 | Doria et al. |
| 4,530,840 | A | 7/1985 | Tice et al. |
| 4,971,971 | A | 11/1990 | Tokunaga et al. |
| 4,985,432 | A | 1/1991 | Tokunaga et al. |
| 5,538,739 | A | 7/1996 | Bodmer et al. |
| 5,576,460 | A | 11/1996 | Buchwald et al. |
| 5,648,539 | A | 7/1997 | Goodbrand et al. |
| 5,648,542 | A | 7/1997 | Goodbrand et al. |
| 5,654,482 | A | 8/1997 | Goodbrand et al. |
| 5,705,697 | A | 1/1998 | Goodbrand et al. |
| 5,723,669 | A | 3/1998 | Goodbrand et al. |
| 5,723,671 | A | 3/1998 | Goodbrand et al. |
| 5,847,166 | A | 12/1998 | Buchwald et al. |
| 5,902,901 | A | 5/1999 | Goodbrand et al. |
| 6,043,370 | A | 3/2000 | Kubo et al. |
| 6,166,226 | A | 12/2000 | Buchwald et al. |
| 6,235,936 | B1 | 5/2001 | Buchwald et al. |
| 6,307,087 | B1 | 10/2001 | Buchwald et al. |
| 6,323,366 | B1 | 11/2001 | Wolfe et al. |
| 6,395,916 | B1 | 5/2002 | Buchwald et al. |
| 6,407,092 | B1 | 6/2002 | Hester et al. |
| 6,465,693 | B2 | 10/2002 | Buchwald et al. |
| 6,541,639 | B2 | 4/2003 | Zhou et al. |
| 6,548,493 | B1 | 4/2003 | Robichaud et al. |
| 6,552,017 | B1 | 4/2003 | Robichaud et al. |
| 6,699,852 | B2 | 3/2004 | Robichaud et al. |
| 6,713,471 | B1 | 3/2004 | Robichaud et al. |

(Continued)

FOREIGN PATENT DOCUMENTS

| | | |
|---|---|---|
| EP | 0 058 481 | 8/1982 |
| EP | 0 856 508 | 8/1998 |

(Continued)

OTHER PUBLICATIONS

Foster ("Deuterium Isotope Effects in the Metabolism of Drugs and Xenobiotics: Implications for Drug Design," Advances in Drug Research, 1985, 14, 1-40).*

Fisher et al. ("The complexities inherent in attempts to decrease drug clearance by blocking sites of CYP-mediated metabolism," Current Opinion in Drug Discovery & Development, 2006, 9, 1, 101-109).*

Avendano et al., "The problem of the existence of C(Ar)-H . . . N Intramolecular Hydrogen Bonds in a Family of 9-Azaphenyl-9H-carbazoles," J. Chem. Soc. Perkin Trans., vol. 2, p. 1547-1555, (1993).

Balbach et al. "Pharmaceutical evaluation of early development candidates the 100 mg-approach", International Journal of Pharmaceutics, vol. 275, p. 1-12 (2004).

(Continued)

*Primary Examiner* — Yong S. Chong
(74) *Attorney, Agent, or Firm* — Hoxie & Associates LLC

(57) ABSTRACT

Use of particular substituted heterocycle fused gamma-carboline compounds as pharmaceuticals for the treatment of agitation, aggressive behaviors, posttraumatic stress disorder or impulse control disorders.

21 Claims, No Drawings

(56) References Cited

U.S. PATENT DOCUMENTS

| | | | |
|---|---|---|---|
| 6,759,554 | B2 | 7/2004 | Buchwald et al. |
| 6,762,329 | B2 | 7/2004 | Marcoux et al. |
| 6,849,619 | B2 | 2/2005 | Robichaud et al. |
| 6,849,640 | B2 | 2/2005 | Ennis et al. |
| 6,867,298 | B2 | 3/2005 | Buchwald et al. |
| 6,888,032 | B2 | 5/2005 | Buchwald et al. |
| 6,946,560 | B2 | 9/2005 | Buchwald et al. |
| 7,026,498 | B2 | 4/2006 | Buchwald et al. |
| 7,071,186 | B2 | 7/2006 | Robichaud et al. |
| 7,081,455 | B2 | 7/2006 | Robichaud et al. |
| 7,109,339 | B2 | 9/2006 | Lee et al. |
| 7,115,784 | B2 | 10/2006 | Buchwald et al. |
| 7,183,282 | B2 | 2/2007 | Robichaud et al. |
| 7,223,879 | B2 | 5/2007 | Buchwald et al. |
| RE39,679 | E | 6/2007 | Robichaud et al. |
| RE39,680 | E | 6/2007 | Robichaud et al. |
| 7,238,690 | B2 | 7/2007 | Robichaud et al. |
| 7,247,731 | B2 | 7/2007 | Buchwald et al. |
| 7,323,608 | B2 | 1/2008 | Buchwald et al. |
| 7,375,226 | B2 | 5/2008 | Jolidon et al. |
| 7,462,641 | B2 | 12/2008 | Igo et al. |
| 7,592,454 | B2 | 9/2009 | Lee et al. |
| 8,309,722 | B2 | 11/2012 | Tomesch et al. |
| 8,598,119 | B2 | 12/2013 | Mates et al. |
| 8,648,077 | B2 | 2/2014 | Tomesch et al. |
| 8,779,139 | B2 | 7/2014 | Tomesch et al. |
| 8,791,138 | B2 | 7/2014 | Seeman et al. |
| 8,993,572 | B2 | 3/2015 | Mates et al. |
| 9,161,061 | B2 | 10/2015 | Mesh-Iliescu et al. |
| 9,168,258 | B2 | 10/2015 | Mates et al. |
| 9,199,995 | B2 | 12/2015 | Tomesch et al. |
| 9,315,504 | B2 | 4/2016 | Tomesch et al. |
| 9,371,324 | B2 | 6/2016 | Mates et al. |
| 9,428,506 | B2 | 8/2016 | Mates et al. |
| 9,586,960 | B2 | 3/2017 | Tomesch et al. |
| 9,616,061 | B2 | 4/2017 | Mates et al. |
| 9,708,322 | B2 | 7/2017 | Li et al. |
| 9,745,300 | B2 | 8/2017 | Mates et al. |
| 9,751,883 | B2 | 9/2017 | Tomesch et al. |
| 9,956,227 | B2 | 5/2018 | Vanover et al. |
| 10,072,010 | B2 | 9/2018 | Li et al. |
| 10,077,267 | B2 | 9/2018 | Mates et al. |
| 10,117,867 | B2 | 11/2018 | Mates et al. |
| 10,322,134 | B2 | 6/2019 | Vanover et al. |
| 10,472,359 | B2 | 11/2019 | Li et al. |
| 10,597,394 | B2 | 3/2020 | Mates et al. |
| 10,654,854 | B2 | 5/2020 | Li et al. |
| 10,688,097 | B2 | 6/2020 | Yao et al. |
| 10,702,522 | B2 | 7/2020 | Mates et al. |
| 10,844,061 | B2 | 11/2020 | Li et al. |
| 10,899,762 | B2 | 1/2021 | Mates et al. |
| 10,960,009 | B2 | 3/2021 | Vanover et al. |
| 10,960,010 | B2 | 3/2021 | Vanover et al. |
| 11,014,925 | B2 | 5/2021 | Li et al. |
| 11,026,951 | B2 | 6/2021 | Mates et al. |
| 11,053,245 | B2 | 7/2021 | Mates et al. |
| 11,096,944 | B2 | 8/2021 | Yao et al. |
| 11,124,514 | B2 | 9/2021 | Mates et al. |
| 11,331,316 | B2 | 5/2022 | Li |
| 11,407,751 | B2 | 8/2022 | Tomesch et al. |
| 11,560,382 | B2 | 1/2023 | Mates et al. |
| 11,680,065 | B2 | 6/2023 | Li et al. |
| 2001/0008942 | A1 | 7/2001 | Buchwald et al. |
| 2004/0034015 | A1 | 2/2004 | Robichaud et al. |
| 2004/0092534 | A1 | 5/2004 | Yam et al. |
| 2004/0127482 | A1 | 7/2004 | Robichaud et al. |
| 2004/0142970 | A1 | 7/2004 | Chung et al. |
| 2008/0069885 | A1 | 3/2008 | Mesens et al. |
| 2008/0132552 | A1 | 6/2008 | Kleinman et al. |
| 2008/0280941 | A1 | 11/2008 | Lourtie et al. |
| 2009/0202631 | A1 | 8/2009 | Yam et al. |
| 2010/0298382 | A1 | 11/2010 | Seeman et al. |
| 2011/0071080 | A1 | 3/2011 | Mates et al. |
| 2011/0112105 | A1 | 5/2011 | Tomesch et al. |
| 2014/0364609 | A1 | 12/2014 | Tomesch et al. |
| 2015/0072964 | A1 | 3/2015 | Mates et al. |
| 2015/0079172 | A1 | 3/2015 | Mates et al. |
| 2015/0080404 | A1 | 3/2015 | Mates et al. |
| 2015/0166540 | A1 | 6/2015 | Mates et al. |
| 2015/0166542 | A1 | 6/2015 | Kjer-Nielsen |
| 2016/0031885 | A1 | 2/2016 | Li et al. |
| 2016/0194325 | A1 | 7/2016 | Tomesch et al. |
| 2016/0194326 | A1 | 7/2016 | Tomesch et al. |
| 2016/0310502 | A1 | 10/2016 | Vanover et al. |
| 2017/0114037 | A1 | 4/2017 | Davis et al. |
| 2017/0189398 | A1 | 7/2017 | Mates et al. |
| 2017/0319580 | A1 | 11/2017 | Yao et al. |
| 2018/0200256 | A1 | 7/2018 | Vanover et al. |
| 2019/0071445 | A1 | 3/2019 | Li et al. |
| 2019/0231780 | A1 | 8/2019 | Yao et al. |
| 2021/0060009 | A1 | 3/2021 | Snyder et al. |

FOREIGN PATENT DOCUMENTS

| | | |
|---|---|---|
| EP | 0 976 732 | 2/2000 |
| EP | 1 245 553 | 10/2002 |
| EP | 1 254 884 | 11/2002 |
| EP | 1 564 671 | 1/2005 |
| EP | 1 539 115 | 6/2005 |
| GB | 1476087 | 6/1977 |
| GB | 2145422 | 3/1985 |
| WO | WO 1994/024125 | 10/1994 |
| WO | WO 1995/013814 | 5/1995 |
| WO | WO 1998/015515 | 4/1998 |
| WO | WO 1998/043956 | 10/1998 |
| WO | WO 1999/043643 | 9/1999 |
| WO | WO 2000/002887 | 1/2000 |
| WO | WO 2000/035419 | 6/2000 |
| WO | WO 2000/077001 | 12/2000 |
| WO | WO 2000/077002 | 12/2000 |
| WO | WO 2000/077010 | 12/2000 |
| WO | WO 2002/085838 | 10/2002 |
| WO | WO 2003/014118 | 2/2003 |
| WO | WO 2004/010981 | 2/2004 |
| WO | WO 2004/013094 | 2/2004 |
| WO | WO 2004/039788 | 5/2004 |
| WO | WO 2004/056324 | 7/2004 |
| WO | WO 2006/034187 | 3/2006 |
| WO | WO 2007/025103 A2 | 3/2007 |
| WO | WO 2008/112280 | 9/2008 |
| WO | WO 2009/114181 | 9/2009 |
| WO | WO 2009/145900 | 12/2009 |
| WO | WO 2011/133224 | 10/2011 |
| WO | WO 2013/155504 | 10/2013 |
| WO | WO 2013/155505 | 10/2013 |
| WO | WO 2013/155506 | 10/2013 |
| WO | WO 2014/145192 | 9/2014 |
| WO | WO 2015/085004 | 6/2015 |
| WO | WO 2015/154025 | 10/2015 |
| WO | WO 2015/154030 | 10/2015 |
| WO | WO 2015/191554 | 12/2015 |
| WO | WO 2017/165755 A1 | 9/2017 |
| WO | WO 2000/064899 | 11/2020 |

OTHER PUBLICATIONS

Bastin et al, "Salt Selection and OptimisationProcedures for Pharmaceutical New Chemical Entities", Organic Process and Research Development, vol. 4, No. 5, p. 427-435 (2000).

Beletskaya et al., "Pd- and Cu-catalyzed selective arylation of benzotriazole," Tetrahedron Letters, vol. 39, pp. 5617-5620, (1998).

Berger et al., "Synthesis of some conformationally restricted analogs of fentanyl," Journal of Medicinal Chemistry, vol. 20, No. 4, p. 600-602. (1977).

Boger et al., "Inverse Electron Demand Diels-Alder Reactions of Heterocyclic Aza Dienes. Studies on the Toal Synthesis of Lavendamycin . . . "J. Org. Chem., vol. 50, p. 5782-5789, (1985).

Borghans, et al., "Animal Models for Posttraumatic Stress Disorder: An Overview of What is Used in Research," World J. Psychiatr., vol. 5, No. 4, pp. 387-396, (2015); DOI: 10.5498/wjp.v5.i4.387.

(56) References Cited

OTHER PUBLICATIONS

Bowman et al., "Synthesis of 1H-quinazoline-4-ones using intramolecular aromatic nucelophilic substitution," Arkivoc, vol. x, p. 434-442 (2003).
Bowman, W.R., et al., "Intramolecular Aromatic Substitution (SRN1) Reactions—Use of Entrainment for the Preparation of Benzothiazoles," Tetrahedron Letters, vol. 23(48), p. 5093-5096, (1982).
Bowman et al., "Copper (1) Catalysed Aromatic Nucleophilic Substitution: A Mechanistic and Synthetic Comparison with the $S_{RN}$ 1 Reaction", Tetrahedron Letters, vol. 25(50) p. 5821-5824, (1984).
Bremner et al., "Neuroimaging of Posttraumatic Stress Disorder", Psychiatric Annals Journal, vol. 28, Issue 8, p. 445-450, (1998).
Bryan-Lluka et al., "Potencies of haloperidol metabolites as inhibitors of the human noradrenaline, dopamine and serotonin transporters in transfected COS-7 cells", Naunyn-Shemiedeberg's Arch Pharmacol, vol. 360, p. 109-115 (1999).
Byrn et al., "Pharmaceutical Solids: A Strategic Approach to Regulatory Considerations", Pharmaceutical Research, vol. 12, No. 7, p. 945-954 (1995).
Caira et al., "Crystalline Polymorphism of Organic Compounds", Topics in Current Chemistry, vol. 198, p. 163-203, (1998).
Crawford et al., "Copper-Catalyzed amidations of bromo substituted furans and thiophenes", Tetrahedron Letters, vol. 43, p. 7365-7368, (2002).
Davis, et al., "ITI-007 demonstrates brain occupancy at serotonin 5-HT2A and dopamine D2 receptors and serotonin transporters using positron emission tomography in healthy volunteers," Psychopharmacology, 232:2863-2872 (2015).
Evindar, G., et al., "Copper- and Palladium-Catalyzed Intramolecular Aryl Guanidinylation: An Efficient Method for the Synthesis of 2-Aminobenzimidazoles", Organic Letters, vol. 5, No. 2, p. 133-136, (2003).
Ezquerra et al., "Efficient Reagents for the Synthesis of 5-, 7-, and 5, 7-Substitued Indoles Starting from Aromatic Amines: Scope and Limitations", J. Org. Chem., vol. 61, p. 5804-5812, (1996).
Fawcett et al., "Posttraumatic Stress Disorder, Stress, and Happiness", Psychiatric Annals Journal, vol. 28, Issue 8, p. 427-428, (1998).
Fee, W.W., et al., "Copper (II)-promoted solvolyses of nickel (II) complexes III. Tetradentate Schiff base ligands containing various diamine segments," Aust. J. Chem., vol. 26, p. 1475-1485, (1973).
Ferreira et al., "Novel synthetic routes to thienocarbazoles via palladium or copper catalyzed amination or amidation of arylhalides and intramolecular cyclization", Tetrahedron, vol. 58, p. 7943-7949, (2002).
Finet et al., "Recent advances in ullmann reaction: copper (II) diacetate catalysed N-,O-,)- and S-arylation involving polycoordinate heteroatomic derivatives," Current Organic Chemistry, vol. 6, p. 597-626, (2002).
Foster, "Acetylcholinesterase inhibitors reduce spreading activation in dementia," Neuropsychologia, vol. 50, p. 2093-2099, (2012).
Friedman et al., "Current and Future Drug Treatment for Posttraumatic Stress Disorder Patients", Psychiatric Annals Journal, vol. 28, Issue 8, p. 464-468, (1998).
Grant, "Polymorphism in Pharmaceutical Solids", Chapter 1, p. 1-10 (1999).
Goodbrand, H.B., et al., "Ligand-Accelerated catalysis of the Ullmann condensation: Application to hole conducting triarylamines," J. Org. Chem., vol. 64, p. 670-674, (1999).
Guillory, "Polymorphism in Pharmaceutical Solids", Chapter 5, p. 183-226 (1999).
Hamann et al., "Systematic Variation of Bidentate Ligands used in Aryl Halide Amination. Unexpected Effects of Steric, Electronic, and Geometric Perturbations", J. Am. Chem. Soc. vol. 120, p. 3694-3703, (1998).
Hackam et al., "Translation of Research Evidence from Animals to Humans", JAMA, 296(14), p. 1731-1732 (2006).
Harbert et al., "Neuroleptic Activity in 5-Aryltetrahydro-y-carbolines", J. Med. Chem., vol. 23, p. 635-643 (1980).
Harvey et al., "Serotonin and Stress: Protective or Malevolent Actions in the Biobehavioral Response to Repeated Trauma?" Annals of the New York Academy of Sciences, vol. 1032, p. 267-272; doi: 10.1196/annals.1314.035 (2004).
Hartwig, J., "Palladium-catalyzed amination of aryl halides: Mechanism and rational catalyst design," Synlett, p. 329-340, (1996).
Hassan, J., et al., "Aryl-aryl bond formation one century after the discovery of the ullmann reaction," Chem. Rev., vol. 102, p. 1359-1469, (2002).
Haynes, "Occurrence of Pharmaceutically Acceptable Anions and Cations in the Cambridge Structural Database", Journal of Pharmaceutical Sciences, vol. 94, No. 10, p. 2111-2120 (2005).
International Search Report issued in International Application No. PCT/US2008/003340, mailed Aug. 8, 2008, 3 pages.
International Search Report issued in International Application No. PCT/US2009/001608, mailed Apr. 27, 2009, 3 pages.
International Search Report issued in International Application No. PCT/US2011/00719, mailed Jul. 5, 2011, 3 pages.
International Search Report issued in International Application No. PCT/US2013/036512, mailed Aug. 19, 2013, 4 pages.
International Search Report issued in International Application No. PCT/US2013/036514, mailed Aug. 16, 2013, 3 pages.
International Search Report issued in International Application No. PCT/US2013/036515, mailed Aug. 13, 2013, 3 pages.
Ito, T., & Watanabe, K., "Studies of organic catalytic reactions. VI. The function of pyridine and copper in the Rosenmund-von Braun reaction," Bulletin of the Chemical Society of Japan vol. 41, p. 419-423, (1968).
Izrayelit et al., "Schizoaffective Disorder and PTSD Successfully Treated With Olanzapine and Supportive Psychotherapy", Psychiatric Annals Journal, vol. 28, Issue 8, p. 424-426, (1998).
Jain et al., "Polymorphism in Pharmacy", Indian Drugs, 23(6), p. 315-316 (1986).
Ji, J., et al., "Selective amination of polyhalopyridines catalyzed by a palladium-xantphos complex," Organic Letters, vol. 5, No. 24, p. 4611-4614, (2003).
Jordan et al., "Tamoxifen: A Most Unlikely Pioneering Medicine", Nature Reviews: Drug Discovery, vol. 2, p. 205-213, (2003).
Kametani et al., "A Novel Synthesis of Indole Derivatives", Heterocycles, vol. 14 (3), p. 277-280, (1980).
Kang et al., "Copper-catalyzed N-arylation of aryl iodides with benzamides or nitrogen heterocycles in the presence of ethylendiamine," Synlett, No. 3, p. 427-430, (2002).
Kessler et al., "Lifetime Prevalence and Age-of-Onset Distributions of DSM-IV Disorders in the National Comorbidity Survey Replication", Arch Gen Psychiatry; vol. 62, p. 593-602, (2005).
Khorana et al., "Gamma-Carbolines: Binding at 5-HT5A Serotonin Receptors", Bioorganic & Medicinal Chemistry, vol. 11, Issue 5, 6, pp. 717-722, p. 718 Table 1, (2003).
Kiyomori et al., "An efficient copper-catalyzed coupling of aryl halides with imidazoles," Tetrahedron Letters, vol. 40, p. 2657-2660, (1999).
Klapars et al., "A general and efficient copper catalyst for the amidation of aryl halides and the N-arylation of nitrogen heterocycles," J. Am. Chem. Soc., vol. 123, p. 7727-7729, (2001).
Klapars et al., "A general and efficient copper catalyst for the amidation of aryl halides," J. Am. Chem. Soc., vol. 124, p. 7421-7428, (2002).
Kondratov et al., "Nucelophilic substitution in the aromatic series. Lv. Reaction of o-nitrochlorobenzene with ammonia in the presence of copper compounds," Zhurnal Organidreskoi Khimii, vol. 51(11), p. 2387-2390, (1979).
Krystal, et al., "Adjunctive Risperidone Treatment for Antidepressant-Resistant Symptoms of Chronic Military Service-Related PTSD," A Randomized Trial. JAMA., 306(5):493-502, (2011).
Kwong et al., "Mild and efficient copper-catalyzed amination of aryl bromides with primary alkylamines," Organic Letters, vol. 5, No. 6, p. 793-796, (2003).
Lebert et al., "Trazodone in Fronto-Temporal Dementia", Research and Practice in Alzheimer's Disease, vol. 11, p. 356-360, (2006).
Lee et al. "Novel, Highly Potent, Selective 5-HT2A/D2 Receptor Antagonists as Potential Atypical Antipsychotics," Bioorg. Med. Chem. Lett. vol. 13, p. 767-770, (2003).

(56) References Cited

OTHER PUBLICATIONS

Li et al., "Discovery of a Tetracyclic Quinoxaline Derivative as a Potent and Orally Active Multifunctional Drug Candidate for the Treatment of Neuropsychiatric and Neurological Disorders", Journal of Medicinal Chemistry, vol. 57, p. 2670-2682 (2014).
Lipschitz et al., "Childhood Posttraumatic Stress Disorder: A Review of Neurobiologic Sequelae", Psychiatric Annals Journal, vol. 28, Issue 8, p. 452-457, (1998).
Liriano, et al. "Ketamine as treatment for post-traumatic stress disorder: a review." Drugs in context, 8:1-7, (2019).
Lopez et al., "Psychiatric Symptoms Vary with the Severity of Dementia in Probable Alzheimer's Disease", J. Neuropsychiatry Clin. Neurosc., vol. 15(3), p. 346-353, (2003).
Louie et al., "Palladium-Catalyzed Synthesis of Arylamines from Aryl Halides, Mechanistic Studies lead to Coupling in the Absence of Tin Reagents", Tetrahedron Letters, vol. 36(21), p. 3609-3612, (1995).
Lounkine et al, "Formal Concept Analysis for the Identification of Molecular Fragment Combinations Specific for Active and Highly Potent Compounds," J. Med. Chem., 51 (17), 5342-5348, (2008).
March et al, Advanced Organic Chemistry; Reactions, Mechanisms and Structures, Fourth Edition, pp. 910-911 (1992).
Marcoux et al., "A general copper-catalyzed synthesis of diaryl ethers," J. Am. Chem. Soc., vol. 119, p. 10539-10540, (1997).
Mohamed et al., "Pharmacotherapy of PTSD in the U.S. Department of Veterans Affairs:diagnostic- and symptom-guided drug selection", J. CLin. Psychiatry, 2008, vol. 69, pp. 959-965.
Morgan et al., "Acoustic Startle in Individuals With Posttraumatic Stress Disorder", Psychiatric Annals Journal, vol. 28, Issue 8, p. 430-434, (1998).
Mulrooney et al., "Recent developments in copper-catalyzed n-arylation with aryl halides," Essay—University of Pennsylvania.
Murakami et al., Chem. Pharm. Bull, vol. 43(8), p. 1281-1286, (1995).
Nagai et al. "Synthesis of 2,3,4,4a,5,9b-hexahydro-1H-pyrido[4,3-b] indole derivatives and their central nervous system activities." Journal of Medicinal Chemistry, vol. 22, No. 6, p. 677-683. (1979).
Nihon rounen igaku zasshi, vol. 48, No. 3, pp. 195-204, (2011 nen). English translation only, 2 pages.
Newman et al., "Solid-state analysis of the active pharmaceutical ingredient in drug products", Drug Discovery Today, vol. 8, No. 9, 898-903 (2003).
Pond et al. "Stereospecific reduction of haloperidol in human tissues". Biochemical Pharmacology, vol. 44 (5), p. 867-871 (1992).
Protective Groups in Organic Synthesis, Third Edition, John Wiley & Sons, Inc., p. 494-505, (1999).
Rackova et al. "Free Radical Scavenging and Antioxidant Activities of Substituted Hexahydropyridoindoles. Quantitative Structure-Activity Relationships." Journal of Medicinal Chemistry, vol. 49, No. 8, p. 2543-2548. (2006).
Ramaswamy, et al., "Failed Efficacy of Ziprasidone in the Treatment of Post-Traumatic Stress Disorder," *Contemporary Clinical Trials Communications*, vol. 2, pp. 1-5, (2016).
Sadighi et al., "A highly active palladium catalyst system for the arylation of anilines," Tetrahedron Letters, vol. 39, p. 5327-5330, (1998).
Savjani et al., "Drug Solubility: Importance and Enhancement Techniques", International Scholarly Research Network Pharmaceutics, vol. 2012, pp. 1-10, (2012).
Semla, et al., "Off-Label Prescribing of Second-Generation Antipsychotics to Elderly Veterans with Posttraumatic Stress Disorder and Dementia," *J. Am. Geriatr. Soc.*, vol. 65, pp. 1789-1795, (2017); DOI: 10.1111/jgs.14897.
Sigel et al., "Tenary Complexes in Solution", Inorganic Chemistry, vol. 13, No. 2, p. 462-465 (1974).
Singhal et al., "Drug polymorphism and dosage form design: a practical perspective", Advanced Drug Delivery Reviews, vol. 56, p. 335-347 (2004).
Skoog, "Principles of Instrumental Analysis, 4th Edition", p. 577 (1992).
Smith, et al., "Oxford Dictionary of Biochemistry and Molecular Biology", Oxford University Press, p. 145, (1997).
Snyder et al., "Functional profile of a novel modulator of serotonin, dopamine, and glutamate neurotransmission", Psychopharmacology, Published online Aug. 2014, DOI 10.1007/s00213-014-3704-1.
Snyder et al., "Functional profile of a novel modulator of serotonin, dopamine, and glutamate neurotransmission", Psychopharmacology, vol. 232, p. 605-621 (2015).
Southwick et al., "Neuroendocrine Alterations in Posttraumatic Stress Disorder", Psychiatric Annals Journal, vol. 28, Issue 8, p. 436-442, (1998).
Sugahara et al., "A Facile Copper-Catalyzed Ullman Condensation: N-Arylation of Heterocyclic Compounds Containing an -NHCO-Moiety", Chem. Pharm. Bull., vol. 45(4), p. 719-721, (1997).
Taragano et al., "A Double-Blind, Randomized, Fixed-Dose Trial of Fluoxetine vs. Amitriptyline in the Treatment of Major Depression Complicating Alzheimer's Disease," Psychosomatics, vol. 38, Issue 3, p. 246-252, (1997).
Tariot, et al., "Memantine Treatment in Patients with Moderate to Severe Alzheimer Disease Already Receiving Donepezil: A Randomized Controlled Trial," JAMA, vol. 291, No. 3, pp. 317-324, (2004).
Vanover, et al., "Dopamine D2 receptor occupancy of lumateperone (ITI-007): a Positron Emission Tomography Study in patients with schizophrenia," *Neuropsychopharmacology* 44:598-605, (2019).
Vanover, et al., "A Novel Approach to Address an Unmet Need in the Treatment of Schizophrenia and Depression: Lumateperone, an Innovative Modulator of Dopamine, Serotonin, and Glutamate," Abstract presented at the American Society of Clinical Psychopharmacology (ASCP) Annual Meeting; May 29-Jun. 1, 2018; Miami, FL.
Wagaw et al., "A palladium-catalyzed method for the preparation of indoles via the Fischer indole synthesis," Journal of the American Chemical Society, vol. 121, No. 44, p. 10251-10263, (1999).
Wennogle, et al., "Activation of NMDA and AMPA Receptors by Lumateperone (ITI-007): Implications for Antidepressant Activity," Abstract presented at the 2017 Collegium Internationale Neuro-Psychopharmacologicum (CINP) Thematic Meeting: Treatment Resistant Depression; Jul. 20-22, 2017; Prague.
Weschules et al., "Acetylcholinesterase Inhibitor and N-Methyl-D-Aspartic Acid Receptor Antagonist Use among Hospice Enrollees with a Primary Diagnosis of Dementia", Journal of Palliative Medicine, vol. 11, No. 5, p. 738-745, (2008).
Wolfe et al., "An improved catalyst system for aromatic carbon-nitrogen bond formation: The possible involvement of bis(phosphine) palladium complexes as key intermediates," JACS, vol. 118, p. 7215-7216, (1996).
Wolfe et al., "Intramolecular palladium-catalyzed aryl amination and aryl amidation," Tetrahedron, vol. 52, No. 21, p. 7525-7546, (1996).
Wolter et al., "Synthesis of N-aryl hydrazides by copper-catalyzed coupling of hydrazides with aryl iodides," Organic Letters, vol. 3, No. 23, p. 3803-3805, (2001).
Yamada et al., "A mild copper-mediated intramolecular amination of aryl halides," Synlett, No. 2, p. 231-234, (2002).
Yang et al., "The development of efficient protocols for the palladium-catalyzed cyclization reactions of secondary amides and carbamates," Organic Letters, vol. 1, No. 1, p. 35-37, (1999).
Yudofsky et al., "Propranolol in the Treatment of Rage and Violent Behavior in Patients with Chronic Brain Syndromes", Am. J. Psychiatry, vol. 138, p. 218-220, (1981).
Zhang et al., "Highly efficient copper-catalyzed N-arylation of alkylamines with aryl iodides using phosphoramidite as ligand", Catalysis Communications, vol. 6, p. 784-787, (2005).
Barman et al., "Newer Antipsychotics: Brexpiprazole, Cariprazine, and Lumateperone: A Pledge or Another Unkept Promise?," World J. Psychiatr., vol. 11, No. 12, p. 1228-38 (2021).
Correll et al., "Efficacy and Safety of Lumateperone for Treatment of Schizophrenia A Randomized Clinical Trial," JAMA Psychiatry, vol. 77, No. 4, p. 349-358 (2020).
Davis, et al., "ITI-007 in the Treatment of Schizophrenia: From Novel Pharmacology to Clinical Outcomes," *Expert Review of Neurotherapeutics*, vol. 16, No. 6, pp. 601-614, (2016).

(56) References Cited

OTHER PUBLICATIONS

Edinoff et al., "Lumateperone for the Treatment of Schizophrenia," Psychopharmacology Bulletin, vol. 50, No. 4, p. 32-59 (2020).
Gramigna, J, "Lumateperone Safe, Effective for Depressive Symptoms Among Patients with Bipolar Disorders," American Society of Clinical Psychopharmacology Annual Meeting, Jun. 2, 2020, 3 pages.
Harvey, "Ziprasidone and Cognition: The Evolving Story," J. Clin. Psychiatry, vol. 64, No. s19, p. 33-39 (2003).
Harvey et al., "Lumateperone Improves Negative Symptoms Related to Emotional Experience (Avolition) in Patient with Schizophrenia," Abstract presented at the American Society of Clinical Psychopharmacology (ASCP) Annual Meeting: May 29-Jun. 1, 2018: Miami, FL.
Hlavinka, E., "Schizophrenia Tx Eases Depression in Bipolar Disorder: Lumateperone Offers Greater Rate of Response, Remission versus Placebo," Medpage Today, 7 pages, (2020); https://www.medpagetoday.com/meetingcoverage/psychcongress/88584.
Intra-Cellular Therapies, Inc., "Corporate Presentation" (Sep. 24, 2019), downloaded from https://ir.intracellulartherapies.com/static-files/93b08960-f01c-4864-aa22-8cadb3539753 (last accessed Mar. 13, 2023).
Liebermann et al., "ITI-007 for the Treatment of Schizophrenia: A 4-Week Randomized, Double-Blind, Controlled Trial," Biological Psychiatry, vol. 79, p. 952-961, (2016).
Press Release, "Intra-Cellular Therapies Announces Additional Results from Phase I/II Clinical Trail for ITI-007 in Healthy Geriatric Subjects and Patients With Dementia," Intra-Cellular Therapies, Press Release Date: Nov. 21, 2014, (http://ir.intracellulartherapies.com/releasedetail.cfm?ReleaseID=884325), accessed on May 31, 2016.
Press Release, "Intra-Cellular Therapies Presents Data on Symptom Improvement by Lumateperone on Negative Symptoms, Depression, and Social Function in Patients with Schizophrenia at the American Society of Clinical Psychopharmacology (ASCP) Annual Meeting," Intra-Cellular Therapies, Press Release Date: May 31, 2018, (https://ir.intracellulartherapies.com/newsreleases/.
Press Release, "Intra-Cellular Therapies Announces Positive Top-Line Results from a Phase 3 Trial of Lumateperone in Patient with Bipolar Depression," Intra-Cellular Therapies, Press Release Date: Jul. 8, 2019.
Vanover et al., Abstracts of the $13^{th}$ International Congress on Schizophrenia (ICOSR) (Apr. 2-6, 2011), Schizophrenia Bull. 37 Suppl. 1., p. 325 (Mar. 2011).
Vanover, K., et al., "ITI-007: A Novel Therapy for the Treatment of Schizophrenia and Related Psychoses," International Clinical Psychopharamcology, vol. 26, e56, 1 page, (2011).
Vyas, P., et al., "An Evaluation of Lumateperone Tosylate for the Treatment of Schizophrenia," Expert Opinion on Pharmacotherapy, vol. 21, No. 2, pp. 139-145, (2020); https://doi.org/10.1080/14656566.2019.1695778.

* cited by examiner

METHOD OF TREATING POST-TRAUMATIC STRESS DISORDER

CROSS REFERENCE TO RELATED APPLICATIONS

This application is a U.S. continuation application of U.S. application Ser. No. 14/394,469, filed on Oct. 14, 2014, which is a national phase application filed under 35 U.S.C. § 371 of International Application No. PCT/US2013/036512, filed on Apr. 14, 2013, which claims priority from U.S. Provisional Application Nos. 61/624,293, 61/624,292 and 61/624,291, all filed on Apr. 14, 2012; and U.S. Provisional Application Nos. 61/671,723 and 61/671,713, both filed on Jul. 14, 2012, the contents of each of which are incorporated by reference in their entireties.

TECHNICAL FIELD

The present invention relates to use of particular substituted heterocycle fused gamma-carbolines as described herein, in free or pharmaceutically acceptable salt forms, as pharmaceuticals and pharmaceutical compositions as primary or adjunct therapy in the treatment of agitation, aggressive behaviors, posttraumatic stress disorder (PTSD) and/or impulse control disorder (ICD) such as intermittent explosive disorder (IED). The compounds disclosed herein can be used in combination with antidepressant compounds, e.g., selective serotonin reuptake inhibitors (SSRI's).

BACKGROUND OF THE INVENTION

Posttraumatic Stress Disorder (PTSD) follows exposure to a traumatic experience involving actual or threatened death or injury or threat to the physical integrity of oneself or others. PTSD includes characteristic symptoms of re-experience, avoidance of stimuli associated with the trauma, and numbing of general responsiveness or hyper-arousal (sleep difficulty, anger, difficulty concentrating, hyper-vigilance or exaggerated startle response) with clinically significant distress or impairment. Lifetime prevalence of PTSD is estimated to be 6.8% among adult Americans, with a prevalence among women more than twice than that among men (Kessler, et al., 2005, Archives of General Psychiatry, 62:593-602). Among combat veterans, at particular risk to develop PTSD, prevalence rates are higher, estimated to be over 25% of Vietnam veterans (Kulka et al., 1990, Trauma and the Vietnam War generation: Report of findings from the National Vietnam Veterans Readjustment Study. New York: Brunner/Mazel), approximately 10% among Gulf War veterans (Kang et al., 2003, American Journal of Epidemiology, 157:141-148), and approximately 14% of Operation Enduring Freedom/Operation Iraqi Freedom (OEF/OIF) veterans (Tanielian and Jaycox, 2008, Invisible Wounds of War: Psychological and Cognitive Injuries, Their Consequences, and Services to Assist Recovery. Santa Monica, CA: RAND Corporation). In addition to the re-experiencing, avoidance, and hyper-arousal cluster of symptoms, PTSD is often associated with dysthymia, sleep disorders, depression, anxiety, substance abuse, bipolar disorder and schizophrenia (Mohamed and Rosenbeck, 2008, J Clin Psychiatry 69:959-965). PTSD is a chronic, costly illness associated with significant long-term disability.

Moreover, no successful dramatic treatment of PTSD has been discovered for the severe, chronic cases of this crippling disorder. A number of articles describing developments in PTSD appear in *Psychiatric Annals* 28:424-468, (1998).

Impulse control disorder (ICD) is characterized by a pathological failure to resist an impulse, drive, or temptation to perform an act that is harmful to the person or to others. One type of ICD is Intermittent Explosive Disorder (IED) which involves violence or rage. There is a loss of control grossly out of proportion to any precipitating psychosocial stresses. Disabling outbursts of rage and violent behavior can be related to chronic brain syndrome associated with irreversible CNS (central nervous system) lesions. Yudofsky et al., *Am. J. Psychiatry* 138:218-220, 1981. Disorders characterized by severe episodic dyscontrol can result from brain dysfunction, e.g., resulting from a failure of modulation of electrical disturbances in the limbic system (amygdala, hippocampus, hypothalamus), temporal lobe epilepsy (TLE), brain lesions or injuries which can have neurological side effects. Other brain dysfunction disorders include motor, personality, or behavior patterns arising from, e.g., neurological impairment in the brain, TLE, viral infections, neurotransmitter disorders, amino acid imbalance, brain tumors, chromosomal abnormalities, metabolic disorders including endocrine disorders, diabetes, and genetic disorders such as disease which involves several genes, and chromosomal disorders. In addition to the traditional ICDs present in the DSM-IV—pathological gambling, trichotillomania, kleptomania, pyromania and intermittent explosive disorder—ICDs may include compulsive—impulsive Internet usage disorder, compulsive—impulsive sexual behaviors, compulsive—impulsive skin picking and compulsive—impulsive shopping.

Poor impulse control, agitation, and aggressive behaviors may be further linked to or co-existent with isolation, depression, and anxiety. It may in be seen in patients suffering from dementia or cognitive impairment, including disorders associated with mild cognition impairment and dementing illnesses including senile dementia, Alzheimer's disease, Pick's disease, frontotemporal dementia, parasupranculear palsy, dementia with Lewy bodies and vascular dementia, as well as in some patients suffering from autism or Asperger's syndrome.

Currently, patients with agitation, PTSD and/or ICD such as IED are usually treated with antidepressants which have limited efficacy and yield extremely low remission rates. New and improved treatments are sorely needed, especially in light of the inadequate evidence to support the efficacy of existing pharmacologic treatments for ICD and PTSD (see, Institute of Medicine (IOM), (2008), "Treatment of posttraumatic stress disorder: an assessment of the evidence." Washington, DC: The National Academic Press). Therefore, there is a need for agents that are useful for the treatment PTSD/ICD either as a primary therapy or as an adjunct therapy to antidepressants.

Substituted heterocycle fused gamma-carbolines are known to be agonists or antagonists of $5\text{-HT}_2$ receptors, particularly $5\text{-HT}_{2A}$ and $5\text{-HT}_{2C}$ receptors, in treating central nervous system disorders. These compounds have been disclosed in U.S. Pat. Nos. 6,548,493; 7,238,690; 6,552,017; 6,713,471; U.S. RE39680, and U.S. RE39679, as novel compounds useful for the treatment of disorders associated with $5\text{-HT}_{2A}$ receptor modulation such as obesity, anxiety, depression, psychosis, bipolar disorder, schizophrenia, sleep disorders, sexual disorders migraine, autism, conditions associated with cephalic pain, social phobias, and gastrointestinal disorders such as dysfunction of the gastrointestinal tract motility. PCT/US08/03340 and U.S. application Ser.

No. 10/786,935 also disclose methods of making substituted heterocycle fused gamma-carbolines and uses of these gamma-carbolines as serotonin agonists and antagonists useful for the control and prevention of central nervous system disorders such as addictive behavior and sleep disorders.

In addition, WO 2009/145900 A1 and WO 2011/133224 A1 teach the use of certain substituted heterocyclic fused gamma-carboline compounds for the treatment of one or more disorders involving the 5-$HT_{2A}$, serotonin transporter (SERT) and/or dopamine D2 pathways.

Although the above-cited references pertaining to substituted heterocyclic fused gamma-carboline compounds teach treatment of disorders associated with psychosis and/or depression, none of these references disclose treatment of PTSD and/or ICD.

SUMMARY OF THE INVENTION

It has been discovered that particular substituted heterocycle fused gamma-carboline compounds (Compounds of Formula I, described herein below) are effective, either alone or as an adjunctive treatment to antidepressants such as serotonin-reuptake inhibitor(s) (SSRI), to treat agitation, aggressive behaviors, PTSD and/or ICD. This is a new and unexpected utility.

Thus, the present invention is directed to a method (Method A) for the treatment of agitation, aggressive behaviors, PTSD and/or ICD, comprising administering to a patient in need thereof an effective amount of the Compound of Formula I:

Formula I

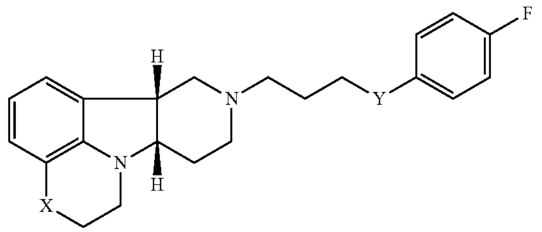

wherein X is —O—, —NH— or —$N(CH_3)$—; and Y is —O—, —C(H)(OH)— or —C(O)—, in free or pharmaceutically acceptable salt form.

In an embodiment, the effective amount is about 1 mg to about 140 mg per dose per day, in another embodiment about 2.5 mg to about 100 mg, in another embodiment about 10 mg to about 100 mg per dose per day, in another embodiment about 10 mg to about 60 mg per dose per day, in another embodiment about 10 mg to about 40 mg per day, in another embodiment about 20 mg to about 40 mg per day, in another embodiment about 40-60 mg per day, in another embodiment, about 1 mg-10 mg per day.

In certain embodiments, the patients may be suffering from other conditions, including psychosis, depression, and/or dementia, for example disorders associated with mild cognition impairment and dementing illnesses including senile dementia, Alzheimer's disease, Pick's disease, frontotemporal dementia, parasupranculear palsy, dementia with Lewy bodies, vascular dementia, Huntington's disease, Parkinson's disease, multiple sclerosis, amyotrophic lateral sclerosis, Down syndrome, elderly depression, Wernicke-Korsakoff's syndrome, corticobasal degenerations, and prion disease, or for example autistic spectrum disorders, e.g., autism or Asperger's syndrome.

Therefore, the invention provides methods as follows:

A method (Method I) for the treatment of PTSD comprising administering to a patient in need thereof an effective amount of a Compound of Formula I:

Formula I

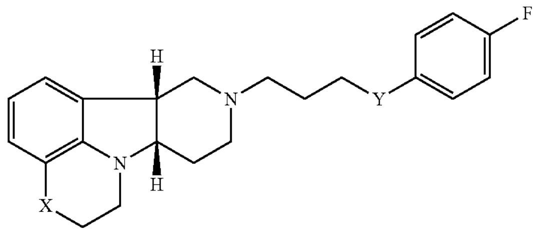

wherein X is O, —NH or —$N(CH_3)$; and Y is —O—, —C(H)(OH)— or —C(O)—, in free or pharmaceutically acceptable salt form.

- 1.1 Method I comprising a compound of Formula I, wherein X is —$N(CH_3)$;
- 1.2 Method I comprising a compound of Formula I, wherein X is —NH;
- 1.3 Method I comprising a compound of Formula I, wherein X is O;
- 1.4 Method I or any of 1.1-1.3, comprising a compound of Formula I, wherein Y is —C(O)—;
- 1.5 Method I or any of 1.1-1.3, comprising a compound of Formula I, wherein Y is —O—;
- 1.6 Method I or any of 1.1-1.3 comprising a compound of Formula I, wherein Y is —C(H)(OH)—;
- 1.7 any of the preceding methods wherein the Compound of Formula I is selected from a group consisting of a compound of Formula I wherein:
  - X is —O— and Y is —C(H)(OH)—,
  - X is —NH— and Y is —C(H)(OH)—,
  - X is —$N(CH_3)$— and Y is —C(H)(OH)—,
  - X is —O— and Y is —C(O)—,
  - X is —O— and Y is —O—,
  - X is —$N(CH_3)$— and Y is —C(O)—,
  - X is —$N(CH_3)$— and Y is —O—,
  - X is —NH— and Y is —C(O)—, and
  - X is —NH— and Y is —O—;
- 1.8 any of the preceding methods wherein X is —O— and Y is —C(O)— in the Compound of Formula I;
- 1.9 any of the preceding methods wherein X is —NH— and Y is —C(H)(OH)— in the Compound of Formula I;
- 1.10 any of the preceding methods wherein X is —$N(CH_3)$— and Y is —C(H)(OH)— in the Compound of Formula I is;
- 1.11 any of the preceding methods wherein X is —O— and Y is —C(O)— in the Compound of Formula I;
- 1.12 any of the preceding methods wherein X is —O— and Y is —O— in the Compound of Formula I;
- 1.13 any of the preceding methods wherein X is —$N(CH_3)$— and Y is —C(O)— in the Compound of Formula I;
- 1.14 any of the preceding methods wherein X is —O— and Y is —C(H)(OH)— in the Compound of Formula I
- 1.15 any of the preceding methods wherein X is —NII— and Y is —C(II)(OII)— in the compound of Formula I;

1.16 any of the preceding methods wherein X is —$N(CH_3)$— and Y is —C(H)(OH)— in the compound of Formula I;

1.17 Method I or any of 1.1-16, wherein said patient is suffering from depression;

1.18 Any of the foregoing methods, wherein the effective amount is 1 mg to 100 mg per day or 10 mg to 100 mg per day, or 10 mg to 50 mg per day, or 10 mg to 40 mg per day, or 1 mg to 10 mg per day, or 10 mg per day, 20 mg per day, or 40 mg per day;

1.19 Any of the foregoing methods wherein a compound of Formula I is administered as an adjunct to one or more different antidepressants, e.g., one or more antidepressants selected from selective serotonin reuptake inhibitors (SSRIs) (e.g., selected from citalopram, escitalopram oxalate, fluoxetine, fluvoxamine maleate, paroxetine, sertraline, dapoxetine), serotonin-norepinephrine reuptake inhibitors (SNRIs) (e.g., selected from venlafaxine, desvenlafaxine, duloxetine, milnacipran, levomilnacipran, sibutramine), and tricyclic antidepressants; triple reuptake inhibitors, anxiolytics, busperone, and trazadone.

1.20 Any of the foregoing methods wherein compound of Formula I is administered as an adjunct to one or more different antidepressants such as SSRIs or an antidepressant is administered as an adjunct to the compound of Formula I;

1.21 The method of 1.19 wherein said one or more antidepressants is selected form SSRI's such as citalopram (Celexa, Cipramil, Emocal, Sepram, Seropram), escitalopram oxalate (Lexapro, Cipralex, Esertia), fluoxetine (Prozac, Fontex, Seromex, Seronil, Sarafem, Fluctin (EUR)), fluvoxamine maleate (Luvox, Faverin), paroxetine (Paxil, Seroxat, Aropax, Deroxat, Paroxat), sertraline (Zoloft, Lustral, Serlain), dapoxetine.

A method (Method II) for the treatment of ICD comprising administering to a patient in need thereof an effective amount of a Compound of Formula I:

Formula I

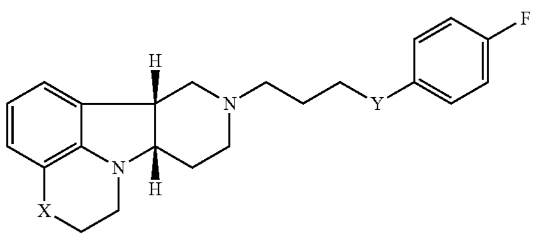

wherein X is —O—, —NH— or —$N(CH_3)$—; and Y is —O—, —C(H)(OH)— or —C(O)—, in free or pharmaceutically acceptable salt form.

The invention further provides Method II as follows:

2.1 Method II comprising a compound of Formula I, wherein X is —$N(CH_3)$;

2.2 Method II comprising a compound of Formula I, wherein X is —NH;

2.3 Method II comprising a compound of Formula I, wherein X is O;

2.4 Method II or any of 2.1-2.3, comprising a compound of Formula I, wherein Y is —C(O)—;

2.5 Method II or any of 2.1-2.3, comprising a compound of Formula I, wherein Y is —O—;

2.6 Method II or any of 2.1-2.3 comprising a compound of Formula I, wherein Y is —C(II)(OII)—;

2.7 any of the preceding methods wherein the Compound of Formula I is selected from a group consisting of a compound of Formula I wherein:

X is —O— and Y is —C(H)(OH)—,
X is —NH— and Y is —C(H)(OH)—,
X is —$N(CH_3)$— and Y is —C(H)(OH)—,
X is —O— and Y is —C(O)—,
X is —O— and Y is —O—,
X is —$N(CH_3)$— and Y is —C(O)—,
X is —N(CII$_3$)— and Y is —O—,
X is —NH— and Y is —C(O)—, and
X is —NH— and Y is —O—;

2.8 any of the preceding methods wherein X is —O— and Y is —C(O)— in the Compound of Formula I;

2.9 any of the preceding methods wherein X is —NH— and Y is —C(H)(OH)— in the Compound of Formula I;

2.10 any of the preceding methods wherein X is —$N(CH_3)$— and Y is —C(H)(OH)— in the Compound of Formula I is;

2.11 any of the preceding methods wherein X is —O— and Y is —C(O)— in the Compound of Formula I;

2.12 any of the preceding methods wherein X is —O— and Y is —O— in the Compound of Formula I;

2.13 any of the preceding methods wherein X is —$N(CH_3)$— and Y is —C(O)— in the Compound of Formula I;

2.14 any of the preceding methods wherein X is —O— and Y is —C(H)(OH)— in the Compound of Formula I 2.15 any of the preceding methods wherein X is —NH— and Y is —C(H)(OH)— in the compound of Formula I;

2.16 any of the preceding methods wherein X is —$N(CH_3)$— and Y is —C(H)(OH)— in the compound of Formula I;

2.17 Method II or any of 1.1-2.16, wherein said patient is suffering from depression;

2.18 Any of the foregoing methods, wherein the effective amount is 1 mg-100 mg per day or 10 mg-100 mg per day, or 10 mg-50 mg per day, or 10 mg-40 mg per day or 1 mg-40 mg per day, or 10 mg per day, 20 mg per day, or 40 mg per day;

2.19 Any of the foregoing methods wherein a compound of Formula I is administered as an adjunct to one or more different antidepressants, e.g., one or more antidepressants selected from selective serotonin reuptake inhibitors (SSRIs) (e.g., selected from citalopram, escitalopram oxalate, fluoxetine, fluvoxamine maleate, paroxetine, sertraline, dapoxetine), serotonin-norepinephrine reuptake inhibitors (SNRIs) (e.g., selected from venlafaxine, desvenlafaxine, duloxetine, milnacipran, levomilnacipran, sibutramine), and tricyclic antidepressants;

2.20 Any of the foregoing methods wherein a compound of Formula I is administered as an adjunct to one or more different antidepressants such as SSRIs or antidepressants such as SSRIs are administered as an adjunct to a compound of Formula I;

2.21 The method of 2.19 wherein said one or more antidepressants is selected from SSRI's such as citalopram (Celexa, Cipramil, Emocal, Sepram, Seropram), escitalopram oxalate (Lexapro, Cipralex, Esertia), fluoxetine (Prozac, Fontex, Seromex, Seronil, Sarafem, Fluctin (EUR)), fluvoxamine maleate (Luvox, Faverin), paroxetine (Paxil, Seroxat, Aropax, Deroxat, Paroxat), sertraline (Zoloft, Lustral, Serlain), dapoxetine;

2.22 Any of the foregoing methods wherein the ICD is IED.

In a particular embodiment of Method A, e.g., Method I et seq. or Method 2, et seq., the patient is a patient who has not responded or has not responded adequately to treatment with another antidepressant or combination of antidepressants, e.g., has not responded adequately to treatment with one or more antidepressants selected from selective serotonin reuptake inhibitors (SSRIs) (e.g., selected from citalopram, escitalopram oxalate, fluoxetine, fluvoxamine maleate, paroxetine, sertraline, dapoxetine), serotonin-norepinephrine reuptake inhibitors (SNRIs) (e.g., selected from venlafaxine, desvenlafaxine, duloxetine, milnacipran, levomilnacipran, sibutramine), and tricyclic antidepressants, e.g., wherein the patient has not responded to SSRIs.

Compounds of the Invention may exist in free or salt form, e.g., as acid addition salts. In this specification unless otherwise indicated language such as "compounds of the Invention", "compounds of the Formula I", "antidepressants", "other therapeutic agents", and the like is to be understood as embracing the compounds in any form, for example free or acid addition salt form, or where the compounds contain acidic substituents, in base addition salt form. The compounds of the Invention are intended for use as pharmaceuticals, therefore pharmaceutically acceptable salts are preferred. Salts which are unsuitable for pharmaceutical uses may be useful, for example, for the isolation or purification of free compounds of the Invention or their pharmaceutically acceptable salts, are therefore also included. Pharmaceutically acceptable salts include, for example, the hydrochloride, mesylate and tosylate salts. Where dosage amounts of salts are given by weight, e.g., milligrams per day or milligrams per unit dose, the dosage amount of the salt is given as the weight of the corresponding free base, unless otherwise indicated.

The invention also provides the foregoing methods, e.g., Method A, e.g., Method I, e.g., any of 1.1-1.21, or Method II, e.g., any of 2.1-2.22, wherein the Compound of Formula I, in free or pharmaceutically acceptable salt form is administered in a composition, wherein said Compound of Formula I in free or pharmaceutically acceptable salt form in admixture with a pharmaceutically acceptable diluent or carrier.

The invention further provides a Pharmaceutical Composition (Composition I) comprising a Compound of Formula I in free or pharmaceutically acceptable salt form, e.g., as described in any of Methods I or 1.1-1.21, in admixture with a pharmaceutically acceptable diluent or carrier for use in any of Methods I, or 1.1-1.21.

The invention further provides a Pharmaceutical Composition (Composition II) comprising a Compound of Formula I in free or pharmaceutically acceptable salt form, e.g., as described in any of Method II, e.g., any of 2.1-2.22, in admixture with a pharmaceutically acceptable diluent or carrier for use in any of Method II, e.g., any of 2.1-2.22.

In another aspect, the invention provides use of a Compound of Formula I or a pharmaceutical composition comprising a compound of Formula I in free or pharmaceutically acceptable salt form as described in Methods I or 1.1-1.21, in the manufacture of a medicament for the treatment of PTSD as described in any of Methods I or 1.1-1.21.

In another aspect, the invention provides use of a compound of Formula I or a pharmaceutical composition comprising a compound of Formula I in free or pharmaceutically acceptable salt form as described in Methods II or 2.1-2.22, in the manufacture of a medicament for the treatment of ICD as described in any of Methods II or 2.1-2.22.

DETAILED DESCRIPTION OF THE INVENTION

The response and remission rates to first-line SSRI treatment of PTSD and IED are poor in veterans; thus, different or augmentation treatment is needed to improve outcomes. In one embodiment, the methods of the present invention using a combination of antidepressant and compound of Formula I, or a compound of Formula I alone, results in a synergistic effect on PTSD and/or ICD. That is, the combination of antidepressant such as SSRI and a compound of Formula I results in a complementary mechanism of action that is better than either class of drug alone. PTSD is listed as diagnosis 309.81 in the Diagnostic and Statistical Manual of Mental Disorders, Fourth Edition, Text Revision (DSM-IV-TR), published by the American Psychiatric Association in 2000. Examples of ICD include compulsive gambling, compulsive shopping, pyromania, kleptomania, trichotillomania, and IED. The majority of the cases of IED occur when the individual is between late adolescence and late twenties. IED is characterized by frequent and often unpredictable episodes of extreme anger or physical outbursts; between episodes there is typically no evidence of violence or physical threat. IED is listed in the DSM-IV-TR as diagnosis 312.34. Specific diagnostic criteria are listed in the DSM-IV-TR for both PTSD and IED.

Methods of Making Compounds of the Invention

The compounds of the formula I and their pharmaceutically acceptable salts may be made using the methods as described and exemplified in any of the following patents or applications: U.S. Pat. Nos. 6,548,493; 7,238,690; 6,552,017; 6,713,471; U.S. RE39680; U.S. RE39679; PCT/US08/03340; U.S. application Ser. No. 10/786,935; WO 2011/133224 A1, and U.S. Provisional Application No. 61/036,069. If not commercially available, starting materials for these processes may be made by procedures, which are selected from the chemical art using techniques which are similar or analogous to the synthesis of known compounds. All references cited herein are hereby incorporated in their entirety by reference.

The words "treatment" and "treating" are to be understood accordingly as embracing prophylaxis and treatment or amelioration of symptoms of disease as well as treatment of the cause of the disease.

The term "patient" may include a human or non-human patient.

Compounds of the Invention refer to Compounds of Formula I, which include:

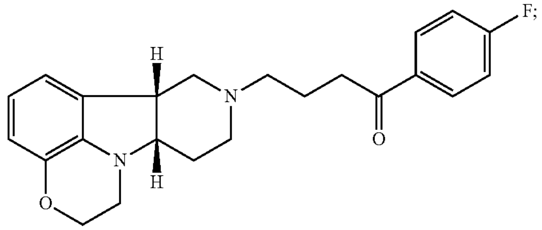

-continued

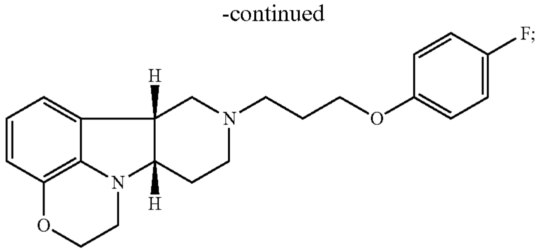

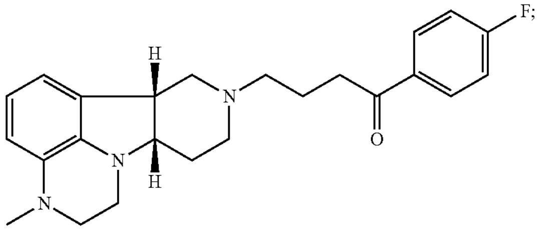

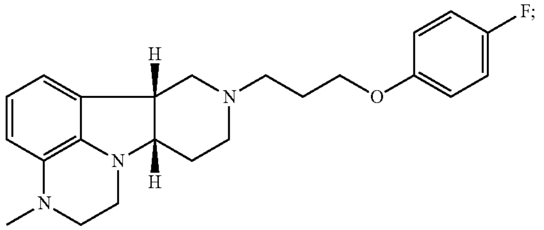

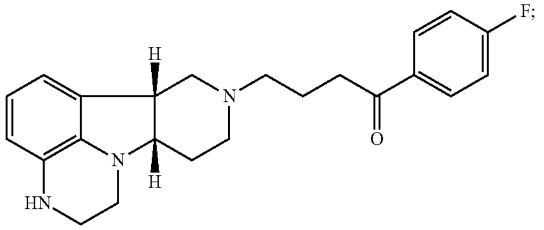

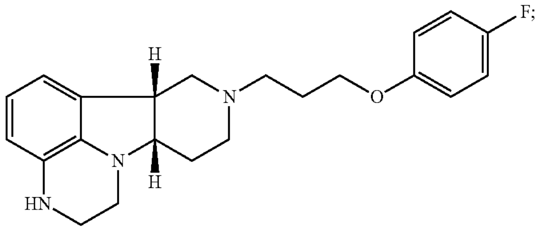

in free or pharmaceutically acceptable salt form. Also, other specific compounds of the invention are where Y is —C(H)(OH)— and X is —O—, —N(H)—, or —N($CH_3$)—. A specific compound of the invention is Compound A which is the compound of Formula I wherein X is —N($CH_3$)— and Y is —C(O)—. The terms "Compounds of Formula I" and "Compounds of the Invention" may be used interchangeably and may be used as a sole therapeutic agent, or they may also be used in combination or for co-administration with other active agents. Also, in the methods of the present invention the phrase "a compound of Formula I" includes more than one of the compounds of Formula I.

Unlike dopamine receptor antagonists, Compounds of Formula I normalize brain dopamine activity, particularly in the prefrontal cortex. The Compounds of Formula I bind to 5-$HT_{2A}$ and dopamine $D_2$ receptors. Compounds of Formula I also exhibit nanomolar binding affinity for SERT compared to known antidepressants. Therefore, in addition to treating PTSD and/or ICD, the compounds of Formula I are useful for the treatment of depression and, in certain embodiments, the treatment of depression in patients suffering from psychosis and for the treatment of psychosis in patients suffering from depression.

In a further embodiment, the invention provides a method of treating PTSD by administering an antidepressant and a compound of Formula I. (Method I-A). In another embodiment, the invention provides a method of treating ICD by administering an antidepressant and a compound of Formula I. (Method II-A). In such methods the antidepressant may be an adjunctive to the compound of Formula I or the compound of Formula I may be an adjunctive to the antidepressant. As used herein the term "adjunctive" refers to any treatment that is used in conjunction with another to increase the chance of cure, or to increase the first treatment's efficacy. In other words, adjunctive therapy acts as an aid to the primary treatment.

In additional embodiments, the invention comprises:

3.1 Method I-A or II-A, wherein the antidepressant is selected from amitriptyline, amoxapine, bupropion, citalopram, clomipramine, desipramine, doxepin, duloxetine, escitaloprame, fluoxetine, fluvoxamine, imipramine, isocarboxazid, maprotiline, mirtazapine, nefazodone, nortriptyline, paroxetine, phenelzine sulfate, protiptyline, sertraline, tranylcypromine, trazodone, trimipramine, and velafaxine;

3.2 Method I-A or II-A, wherein the antidepressant(s) is a selective serotonin reuptake inhibitor (SSRI);

3.3 Method I-A or II-A or 3.1, wherein the SSRI compound is selected from the group consisting of citalopram, escitalopram oxalate, fluoxetine, fluvoxamine maleate, paroxetine, sertraline, and dapoxetine.

The combination compositions of the invention can include mixtures of the combined drugs, as well as two or more separate compositions of the drugs, which individual compositions can be, for example, co-administered together to a patient at the same of different times.

Dosages employed in practicing the present invention will of course vary depending, for example, on the particular disease or condition to be treated, the particular compound of the Invention used, the mode of administration, and the therapy desired. Unless otherwise indicated, an amount of the Compound of the Invention for administration (whether administered as a free base or as a salt form) refers to or is based on the amount of the compound of the Invention in free base form (i.e., the calculation of the amount is based on the free base amount). Compounds of the Invention may be administered by any suitable route, including orally, parenterally or transdermally, but are preferably administered orally.

The dosages of a compound of Formula I and/or the antidepressant of Method I-A and II-A can be the same as or lower than the approved dosage for the drug, the clinical or literature test dosage or the dosage used for the drug as a monotherapy. For example the daily dosage of compound of Formula I to be administered in combination with an antidepressant is about 1 mg to about 140 mg, in another embodiment about 1 mg to about 100 mg, in another embodiment about 10 mg to about 100 mg, in another embodiment about 10 mg to about 50 mg, in another embodiment about 10 mg to about 40 mg, in another embodiment about 20 mg to about 40 mg and in another embodiment about 1 mg to about 10 mg. The amount of antidepressant to be administered in combination with the compound of Formula I is about 0.01 mg to about 2000 mg, in another embodiment about 0.1 mg to about 200 mg, in another embodiment about 10 mg to about 200 mg. In particular embodiments, the second therapeutic agent, that is antidepressant SSRI of Method I-A and II-A is sertraline and the daily dosage of sertraline is between about 20 mg and 100 mg.

In a specific embodiment, the dosages of a compound of Formula I and/or the second therapeutic agents of Method I-A and II-A are lower than when used in a monotherapy. Therefore, in a particular embodiment, the daily dosage of a compound of Formula I is lower than 100 mg once daily, or less than 50 mg, or less than 40 mg, or less than 30 mg, or less than 20 mg, or less than 10 mg. In another preferred embodiment, the dosages of both the Compound of Formula I and the antidepressant agent of Method I-A and II-A are lower than the dosages used for the individual drug as a monotherapy. Therefore, in a particular embodiment, for example, Method I-A or II-A comprises administering (1) a Compound of Formula I at a dosage lower than 100 mg once daily, preferably less than 50 mg, more preferably less than 40 mg, still more preferably less than 30 mg, still more preferably less than 20 mg, still more preferably less than 10 mg; and (2) antidepressant, for example a SSRI such as sertaline, at a daily dosage of less than 50 mg, more preferably, less than 20 mg, still more preferably, less than 10 mg, most preferably less than 6 mg, in free or pharmaceutically acceptable salt form.

In some embodiments, the methods of the invention also encompass additional methods for treating other disorders. Such additional disorders include, but are not limited to, sleep disorders associated with psychosis, e.g., sleep disorders associated with schizophrenia or Parkinson's disease.

More specific disorders which may co-exist with agitation, ICD and/or PTSD and may be treated using the methods of the invention include (a) psychosis with a co-morbid disorder of depression and/or sleep disorder; (b) depression with a co-morbid disorder of psychosis; (c) sleep disorder in patients suffering from psychosis, Parkinson disease, and/or depression; (d) disorders associated with cognition impairment, including mild cognition impairment, and dementing illnesses including senile dementia, Alzheimer's disease, Pick's disease, frontotemporal dementia, parasupranculear palsy, Parkinson's dementia, dementia with Lewy bodies, vascular dementia, Huntington's disease, Parkinson's disease, multiple sclerosis, amyotrophic lateral sclerosis, Down syndrome, elderly depression, Wernicke-Korsakoff's syndrome, corticobasal degenerations, and prion disease; or (e) any combinations thereof. Optionally, the compounds of Formula I may be simultaneously, sequentially, or contemporaneously administered with another antidepressant (Methods I-A and II-A), or additional therapeutics may also be administered in either Methods, I, II, I-A, or II-A, for example, anti-psychotic, hypnotic agents, and/or agents used to treat Parkinson's disease or mood disorders. In another example, side effects may be reduced or minimized by administering a compound of Formula I in combination with one or more second therapeutic agents in free or salt form, wherein the dosages of the second therapeutic agent(s) or both compound of Formula I and the second therapeutic agents are lower than if the agents/compounds are administered as a monotherapy.

As mentioned above, dosages of the compound of the invention will vary depending, e.g. on the particular disease or condition to be treated, the particular Compound of the Invention used, the mode of administration, the therapy desired, as well as specific patients' needs, other therapeutic agents administered, disorders to be treated, and the like. Other daily doses contemplated to be within the scope of the invention are about 1 mg, 2 mg, 2.5 mg, 3 mg, 4 mg, 5 mg, 10 mg, 20 mg, 30 mg, 40 mg, or 50 mg. If additional therapeutic agents are used in Methods I, II, I-A, or II-A, the daily doses of such agents can vary considerably depending the specific agent chosen as well as other factors mentioned above, for example, daily doses of about 0.001 mg to about 2000 mg, 0.1 mg to about 200 mg, 1 mg to about 100 mg, 10 mg to about 100 mg, 10 mg to about 50 mg, 20 mg to about 50 mg, and the like.

Other therapeutic agents which can be optionally administered to a patent in need thereof include compounds that modulate GABA activity (e.g., enhances the activity and facilitates GABA transmission), a GABA-B agonist, a 5-HT modulator (e.g., a $5\text{-HT}_{1A}$ agonist, a $5\text{-HT}_{2A}$ antagonist, a $5\text{-HT}_{2A}$ inverse agonist, etc.), a melatonin agonist, an ion channel modulator (e.g., blocker), a serotonin-2 antagonist/reuptake inhibitor (SARIs), an orexin receptor antagonist, an H3 agonist, a noradrenergic antagonist, a galanin agonist, a CRH antagonist, human growth hormone, a growth hormone agonist, estrogen, an estrogen agonist, a neurokinin-1 drug, and an antipsychotic agent, e.g., an atypical antipsychotic agent, in free or pharmaceutically acceptable salt form.

The term "GABA" refers to gamma-aminobutyric acid. The GABA compounds are compounds which bind to the GABA receptor, and include, but are not limited to one or more of doxepin, alprazolam, bromazepam, clobazam, clonazepam, clorazepate, diazepam, flunitrazepam, flurazepam, lorazepam, midazolam, nitrazepam, oxazepam, temazapam, triazolam, indiplon, zopiclone, eszopiclone, zaleplon, Zolpidem, gabaxadol, vigabatrin, tiagabine, EVT 201 (Evotec Pharmaceuticals) or estazolam.

Other optional therapeutic agents are $SHT_{2A}$ antagonists such as ketanserin, risperidone, eplivanserin, volinanserin (Sanofi-Aventis, France), pruvanserin, pimavanserin (ACP-103), MDL 100907 (Sanofi-Aventis, France), HY10275 (Eli Lilly), APD125 (Arena Pharmaceuticals, San Diego, CA), or AVE8488 (Sanofi-Aventis, France).

Still other optional therapeutic agents include pizotifen.

Other optional therapeutic agents are $SHT_{1A}$ agonists such as repinotan, sarizotan, eptapirone, buspirone or MN-305 (MediciNova, San Diego, CA).

Other optional compounds are melatonin agonists such as melatonin, ramelteon (ROZEREM®, Takeda Pharmaceuticals, Japan), VEC-162 (Vanda Pharmaceuticals, Rockville, MD), PD-6735 (Phase II Discovery or agomelatine.

Other optional therapeutic agents are ion channel blockers such as lamotrigine, gabapentin or pregabalin.

Other optional therapeutic agents are orexin receptor antagonists such as orexin, a 1,3-biarylurea, SB-334867-a (GlaxoSmithKline, UK), GW649868 (GlaxoSmithKline) or a benzamide derivative, for example.

Other optional therapeutic agents are serotonin-2 antagonist/reuptake inhibitors (SARI) such as Org 50081 (Organon—Netherlands), ritanserin, nefazodone, serzone or trazodone.

Other optional therapeutic agents are neurokinin-1 drugs such as Casopitant (GlaxoSmithKline).

Specific examples of additional therapeutic agents include modafinil, armodafinil, doxepin, alprazolam, bromazepam, clobazam, clonazepam, clorazepate, diazepam, flunitrazepam, flurazepam, lorazepam, midazolam, nitrazepam, oxazepam, temazapam, triazolam, indiplon, zopiclone, eszopiclone, zaleplon, zolpidem, gabaxadol, vigabatrin, tiagabine, EVT 201 (Evotec Pharmaceuticals), estazolam, ketanserin, risperidone, eplivanserin, volinanserin (Sanofi-Aventis, France), pruvanserin, MDL 100907 (Sanofi-Aventis, France), HY10275 (Eli Lilly), APD125 (Arena Pharmaceuticals, San Diego, CA), AVE8488 (Sanofi-Aventis, France), repinotan, sarizotan, eptapirone, buspirone, MN-305 (MediciNova, San Diego, CA), melatonin, ramelteon (ROZEREM®, Takeda Pharmaceuticals, Japan), VEC-162 (Vanda Pharmaceuticals, Rockville, MD), PD-6735 (Phase II Discovery), agomelatine, lamotrigine, gabapentin, pregabalin, orexin, a 1,3-biarylurea, SB-334867-a (GlaxoSmithKline, UK), GW649868 (GlaxoSmithKline), a benzamide derivative, Org 50081 (Organon—Netherlands), ritanserin, nefazodone, serzone, trazodone, Casopitant (GlaxoSmithKline), amitriptyline, amoxapine, bupropion, citalopram, clomipramine, desipramine, doxepin, duloxetine, escitaloprame, fluoxetine, fluvoxamine, imipramine, isocarboxazid, maprotiline, mirtazapine, nefazodone, nortriptyline, paroxetine, phenlzine sulfate, protiptyline, sertraline, tranylcypromine, trazodone, trimipramine, velafaxine, chlorpromazine, haloperidol, droperidol, fluphenazine, loxapine, mesoridazine molidone, perphenazine, pimozide, prochlorperazine promazine, thioridazine, thiothixene, trifluoperazine, clozapine, aripiparazole, olanzapine, quetiapine, risperidone, ziprasidone and paliperidone, asenapine, lurasidone, iloperidone and cariprazine, in free or pharmaceutically acceptable salt form.

The compounds to be administered in the methods of the present invention can be in the form of free acid or free base or as pharmaceutically acceptable salts. The phrase "pharmaceutically acceptable salts" refers to derivatives of the above disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the compounds to be used in the methods of the invention can be synthesized from the parent compound which contains a basic or acidic moiety by conventional chemical methods. Generally, such salts can be prepared by reacting the free base forms of these compounds with a stoichiometric amount of the appropriate acid in water or in an organic solvent, or in a mixture of the two; generally, nonaqueous media like ether, ethyl acetate, ethanol, isopropanol, or acetonitrile are preferred. Further details for the preparation of these salts, e.g., toluenesulfonic salt in amorphous or crystal form, may be found in PCT/US08/03340 and/or U.S. Provisional Appl. No. 61/036,069 and WO 2009/114181.

Pharmaceutical compositions comprising the compounds of the invention may be prepared using conventional diluents or excipients and techniques known in the galenic art. For example the compounds can be administered in a wide variety of different dosage forms, i.e., they may be combined with various pharmaceutically-acceptable inert carriers in the form of tablets, capsules, lozenges, troches, hard candies, powders, sprays, aqueous suspension, injectable solutions, elixirs, syrups, and the like.

For oral administration, the pharmaceutical compositions may take the form of, for example, tablets or capsules prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium phosphate); lubricants (e.g. magnesium stearate, talc or silica); disintegrants (e.g. potato starch or sodium starch glycolate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, methyl cellulose or hydrogenated edible fats); emulsifying agents (e.g. lecithin or acacia); non-aqueous vehicles (e.g. almond oil, oily esters or ethyl alcohol); and preservatives (e.g. methyl or propyl p-hydroxybenzoates or sorbic acid).

For buccal administration the composition may take the form of tablets or lozenges formulated in conventional manner.

The active compounds may be formulated for parenteral administration by injection, including using conventional catheterization techniques or infusion. Formulations for injection may be presented in unit dosage form, e.g. in ampules or in multi-dose containers, with an added preservative. The compositions may take such forms as suspensions, solutions or emulsions in oily or aqueous vehicles, and may contain formulating agents such as suspending, stabilizing and/or dispersing agents. Alternatively, the active ingredient may be in powder form for reconstitution with a suitable vehicle, e.g. sterile pyrogen-free water, before use.

The active compounds may also be formulated in rectal compositions such as suppositories or retention enemas, e.g., containing conventional suppository bases such as cocoa butter or other glycerides.

For intranasal administration or administration by inhalation, the active compounds are conveniently delivered in the form of a solution or suspension from a pump spray container that is squeezed or pumped by the patient or as an aerosol spray presentation from a pressurized container or a nebulizer, with the use of a suitable propellant, e.g. dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. The pressurized container or nebulizer may contain a solution or suspension of the active compound. Capsules and cartridges (made, for example, from gelatin) for use in an inhaler or insufflator may be formulated containing a powder mix of an active compound and a suitable powder base such as lactose or starch. When aqueous suspensions and/or elixirs are desired for oral administration, the essential active ingredient(s) therein may be combined with various sweetening, or flavoring agents, coloring matter or dyes and, if so desired, emulsifying and/or suspending agents as well, together with such diluents as water, ethanol, propylene glycol, glycerin and various like combinations thereof.

The following example is to illustrate the invention but should not be interpreted as a limitation thereon.

EXAMPLES

Example 1: Open Label Study of Compound a for Treatment of PTSD

A single-site, prospective, open label pilot study is performed of Compound A (Formula I wherein X is —$N(CH_3)$— and Y is —C(O)—; tosylate salt) as adjunctive treatment to the selective serotonin-reuptake inhibitor (SSRI) in veterans with non-remitting posttraumatic stress disorder.

Research Design and Methods

This study focuses on subjects who fail to remit to sertraline, the first-line FDA indicated medication for PTSD.

Adjunctive Treatment Pilot Study Design Overview:

Male and female subjects (n=20) from Active Duty, Reserves, National Guard and/or Veterans between the ages of 19 and 65 years, inclusive, with a diagnosis of non-remitting PTSD as defined by failing an adequate trial of a SSRI are prospectively treated with adjunctive Compound A for 12 weeks.

Methods to Obtain a Sample of Volunteers:

Participants are recruited from outpatient clinics, residential treatment programs, and nearby US Military Reserve or Active Units, as potential subjects present for medical/psychiatric evaluation. Of the 16,000 total patients in the network studied, approximately 18% (n=2880) have a diagnosis of PTSD; 88% are male, ~59% Caucasian and 41% minorities. Of the 1,200 or more OIF/OEF veterans treated at TVAMC, 63% have a mental illness diagnosis and 42% have PTSD.

Inclusion Criteria:

(1) Signed informed consent (i.e. subject can read and understand the procedures, alternatives, risks and benefits and agrees to visit frequency)
(2) Male or female; any race or ethnic origin
(3) ≥19 to 65 years of age
(4) Served in US military
(5) Diagnosis of PTSD by Mini-International Neuropsychiatric Inventory (MINI) and Clinician Administered PTSD Scale (CAPS) using Rule of Fours and total CAPS score greater or equal to 45
(6) Inadequate response to standard SSRI therapy (>6 wk duration; citalopram 40 mg/d, sertraline 150 mg/d, fluoxetine 40 mg/d, paroxetine 40 mg/d, or equivalent)
(7) CAPS score≥45 for the past week prior to randomization (defines an inadequate response)
(8) At least moderate severity on CGI-Severity scale (defines an inadequate response)
(9) No substance use disorders (except for nicotine and caffeine) in the previous 1 month
(10) Free of other psychotropic medications (mood stabilizers, neuroleptics, benzodiazepines, non-SSRI medications, prazosin) for 2 wks prior to randomization. Subjects can be tapered off excluded medication if not responding to or having intolerable side effects to the medication.

Exclusion Criteria (1) Lifetime history of bipolar I, schizophrenia, schizoaffective disorders (assessed by the MINI)
(2) Actively considering plans of suicide or homicide (assessed by clinical interview)
(3) Psychotic symptoms that in the investigator's opinion impair the subject's ability to give informed consent or make it unsafe for subject to be maintained without a neuroleptic
(4) Severe cognitive disorder (dementia, severe TBI)
(5) Nonresponse to >3 adequate trials of psychotropic medication(s), i.e. treatment-refractory
(6) A contraindication to the use of Compound A or SSRI
(7) Pregnant women or women planning to become pregnant or breastfeed during the study
(8) Clinically significant unstable or severe medical condition that would contraindicate study participation or expose them to an undue risk of a significant adverse event, including but not limited to: unstable or severe hepatic, renal, respiratory, cardiovascular, endocrine, neurologic, or hematologic disease; hypo- or hyperthryoidism, unless the condition has been stabilized for 3 months; or a history of seizures (except for a single childhood febrile seizure, post-traumatic, or alcohol withdrawal). The following are exclusionary: platelets<75,000/mm; hemoglobin<9 g/dL; neutrophils, absolute<1000/mm; SGOT>3× upper limit; SGOT>3× upper limit; creatine>2 mg/dL; diastolic BP<60 or >110 mmHg; EKG QTc>475 msec.
(9) In regard to vulnerable patient populations, persons with dementia, minors (<age 19), the elderly (>age 65), prisoners and the terminally ill are excluded.

Screening Procedures:

After providing signed informed consent, 1-14 day screening and baseline assessment includes a psychiatric and general medical evaluation, psychiatric history, family psychiatric history, psychotropic medication history, demographics, disability status, a diagnostic evaluation (the MINI and the CAPS), an inventory of general medication conditions, a physical, EKG, and laboratory tests (complete blood count, liver and thyroid function tests, blood chemistry, urinalysis, urine screen for drugs of abuse, and fasting glucose and lipid profile). Women of child-bearing potential have a negative urine pregnancy test.

Study Medication:

After eligibility is determined, the subject receives Compound A. Compound A is initiated at 20 mg/day for the first 7 days, then increased to 40 mg/d. The target dose is 40 mg/d, but the dose is reduced to 20 mg/d as needed due to side effects. The study medication is stored and dispensed by the TVAMC pharmacy. The baseline SSRI medication is continued throughout the 12-wks study.

Concomitant Medication and Psychotherapy:

Except for the SSRI and study medication, no other psychotropic medications are allowed during the study (including mood stabilizers, other antidepressants, neuroleptics, benzodiazepines, prazosin). Pain medications (narcotics, gabapentin, acetaminophen, nonsteroidal anti-inflammatory agents) for pain conditions are allowed as long as doses are stable for 4 wks prior to randomization. Due to the potential confounding therapeutic effects of some types of psychotherapy, concurrent cognitive behavioral therapy, cognitive processing therapy or exposure therapy is not allowed during the study.

Baseline Procedures and Follow-up Assessments:

Subjects are assessed by the investigators or trained clinical research coordinators with telephone contacts every two weeks and the assessments (indicated in the Table below) every four weeks.

Mini-International Neuropsychiatric Inventory (MINI):

A structured clinician-administered interview that assesses current and lifetime DSM-IV Axis I disorders. The MINI has good reliability and validity. Selected for its reduced burden on the research participant, the MINI takes ~30 min to administer compared to 45-60 min for the Structured Clinical Interview for DSM-IV.

Clinician Administered PTSD Scale (CAPS; Primary Outcome):

A structured clinician-administered interview is used to assess frequency and intensity of 17 symptoms of PTSD. The CAPS is further subdivided into three clusters to allow scoring for Criterion B (re-experiencing), Criterion C (avoidant behaviors) and Criterion D (hyper-arousal). CAPS is advantageous in that: 1) it is a standard rating scale in PTSD studies; 2) it allows comparison of the results of the this study to studies of other medications (i.e. SSRIs) for PTSD that used the CAPS, and 3) it gives reliable scores for the 3 PTSD symptom clusters for more detailed analysis of the PTSD B, C, and D clusters.

Quick Inventory of Depressive Symptomatology—Self Report (QIDS-C):

A 16-item self report rating scale for depression used extensively in clinical trials; has good internal consistency, reliability, and is sensitive to change. An assessment of depression is selected because depression occurs frequently in PTSD patients.

Positive and Negative Syndrome Scale (PANSS):

A 30-item clinician-administered scale to assess the positive and negative syndromes in psychotic disorders; good reliability and validity; sensitive to treatment changes.

Clinical Global Impression-Severity & Clinical Global Impression-Improvement (CGI-S/CGI-I):

7-point clinician scales that are used in RCTs to measure severity of illness & improvement.

Self Report Scales:

Pittsburgh Sleep Quality Index (PSQI): A frequently used self-rated sleep questionnaire that has been validated in healthy and psychiatric patients with an addendum has been developed to assess sleep disturbances more specific to PTSD. Sheehan Disability Scale (SDS): a 3-item of the degree to which psychiatric symptoms are disruptive of occupational, family/home, and social function; has high internal consistency (0.89), good validity, and is sensitive to change. Intent-to-Attend: a 2-item scale that asks the subject at baseline "How likely is it that you will complete the study?" and asks the subjects at follow-up "How likely is it that you will attend next assessment session?" and scores from zero to 10. These data could change non-ignorable dropout to ignorable or be used clinically to discuss identifiable barriers and encourage follow-up. Treatment Satisfaction Questionnaire for Medication (TSQM): a 14-item Likert-type self-report; psychometrically valid; measures major dimensions of patients' satisfaction with medication.

Adverse Event Monitoring: Frequency, Intensity, and Burden of Side Effects Rating (FIBSER):

A self-report; measures side effect global frequency, intensity, and overall burden. Abnormal Involuntary Movement Scale (AIMS):65 12-item clinician admin scale that assesses the presence and severity of dyskinetic movements, used widely for assessment of tardive dyskinesia; has established inter-rater reliability. Barnes Akathisia Scale (BAS): A 4-item clinician admin validated scale to assess presence and severity of drug-induced akathisia. Simpson-Angus Scale (SAS): A 10-item validated scale to assess presence and severity of dystonia or Parkinsonism symptoms. Sheehan Suicidality Tracking Scale (SSTS), is an 8-item self-report scale; tracks treatment-emergent suicidal ideation (items 2, 3, 4 plus score from item 5 if <1) and behaviors (items 6, 7a, 8, plus item 5 if >1); sensitive to change in frequency or intensity of suicidal thoughts or behaviors over time; maps directly to the suicidality classification coding system used by the FDA. At each visit, the subject completes the SSRS and one of the investigators reviews it. Positive endorsements are handled by the investigator (see suicide prevention plan).

| Activity | Time min | Wk 0** | Wk 4 | Wk 8 | Wk 12 |
|---|---|---|---|---|---|
| Consent and HIPAA | 20 | X | | | |
| MINI Diagnostic Interview | 30 | X | | | |
| Inventory of Medical Conditions | 15 | X | | | |
| Physical/EKG | 15 | X | | | X |
| Labs/UDS | 15 | X | | | X |
| Pregnancy Test* | 1 | X | | | X |
| VS/Wt/Ht | 5 | X | X | X | X |
| Substance Use Inventory | 1 | X | X | X | X |
| Concomitant Medications | 5 | X | X | X | X |
| Study Medication Adherence | 5 | | X | X | X |
| CAPS-SX | 30 | X | X | X | X |
| QIDS-SR | 10 | X | X | X | X |
| CGI-S, CGI-I | 1 | X | X | X | X |
| PSQI/SDS self-reports | 10 | X | X | X | X |
| PANSS | 20 | X | | | X |
| Intent to Attend self report | 1 | X | X | X | X |
| Adverse Events Assessment | 5 | | X | X | X |
| FIBSER/TSQM self report | 5 | | X | X | X |
| SAS/BAS/AIMS clinician admin | 10 | X | X | X | X |
| Suicidality Assessment (SSTS) | 5 | X | X | X | X |
| Time (min) | 210 | 200 | 98 | 99 | 124 |

Rater Reliability and Training:

Procedures for training research staff are outlined by Tracy K., et al. (1997). "Inter-rater reliability issues in multicenter trials, Part I: theoretical concepts and operational procedures used in Department of VA CSP #394." Psychopharm Bull 33:1:53-57; which are specific guidelines for establishing and preserving inter-rater reliability. Past inter-rater reliability coefficient ranged from 0.75 to 1.0 for the CAPS total and subscales. Prior to study initiation, training for all scales are conducted and inter-rater reliability coefficients in the range of 0.90 to 0.95 are established and will be repeated annually. As much as possible, each subject is evaluated by the same rater during the study.

Suicide Prevention Plan:

Subjects are evaluated at every 2 weeks by phone (or more frequently if needed) and every 4 weeks in clinic. The subject completes the SSTS self report at the clinical visit and the SSTS is reviewed by the MD or Nurse Practitioner. The investigator explores all positive endorsements with the subject and judges the clinical state and risk of suicide. At baseline, the investigator and subject agree on a detailed suicide prevention plan, which includes 24 hr access to one of the investigators (paging) in the event of suicidal thoughts, plans or behaviors, 24 hr access to the VAMC emergency room, knowing the VA suicide prevention crisis and VA suicide prevention coordinators' phone numbers (cards and flyers are given to subjects), identifying a significant other who can assist during a crisis, removal of all lethal weapons from the immediate access of the subject, and subject's agreement to abstain from drugs and alcohol. If positive endorsements are made on the SSTS, the investigator reviews and modifies the suicide prevention plan with the subject. Should the investigator deem the subject to be at heightened risk of suicide, the subject is treated in the most clinically appropriate setting (outpatient, residential or inpatient), the study medication may be discontinued and other treatments provided, and appropriate AE or SAE reports are filed with IRB.

Adverse Event Monitoring:

In addition to treatment-emergent suicidal thoughts and behaviors described above, the patients are monitored for all possible side effects and adverse events on a regular basis (i.e. face-to-face monthly clinic visits with telephone contact in the intervening weeks). Laboratory tests and EKG are repeated at week 12 to evaluate medical and/or cardiac outcomes. Adverse events, weight, and vital signs are evaluated at each visit. All adverse events are recorded at each visit (description, severity, relationship to study medication, intervention, date onset, date resolution) regardless of relationship to study medication. Serious adverse events (as defined by CRF 312.32) that are unanticipated and related to the study medication are expeditiously reported to the IRB and all regulatory agencies.

Physical Risks:

Side effects are listed in the informed consent and reviewed carefully with the subject. Most adverse events of Compound A are mild to moderate and include headache, dizziness, postural tachycardia, dry mouth, gastrointestinal complaints, and somnolence. Importantly, Compound A lacks potent off-target interactions that may be associated with unwanted side effects. At doses where target receptors are engaged, Compound A is not likely to exhibit sedation associated with H1 antagonism (H1 Ki>1000 nM), weight gain, or metabolic liability associated with H1 or 5-HT2C receptor antagonism (5-HT2C Ki=173 nM). Compound A has no affinity for muscarinic receptors and is not anticipated to be associated with anticholingeric side effects. The closest off-target activity is adrenergic alpha 1A (Ki=73 nM). To date, this has not been associated with any cardiovascular side effects, such as postural hypotension, but subjects are closely monitored.

Compound A is safe and well-tolerated across a range of doses (1-140 mg) in healthy volunteer and clinical populations. A randomized, double-blind, placebo-controlled single oral dose escalation study to demonstrate the safety, tolerability and pharmacokinetics of Compound A in 30 young, healthy volunteers demonstrated that single oral doses of 2.5 mg, 5.0 mg, 10.0 mg, 20.0 mg and 30.0 mg are safe and tolerated in healthy male volunteers. There are no serious adverse events in this study. There are no dose-related clinically relevant changes in vital signs or clinical laboratory. There are no significant increase in QTc and no clinically significant changes in any 12-lead ECG or 24-hour Holter-ECG. Most adverse events are mild to moderate, and included headache, dizziness, postural tachycardia, dry mouth, gastrointestinal complaints, and somnolence. In another placebo-controlled study in 24 healthy male volunteers, multiple oral doses of 5, 10 and 20 mg Compound A once daily for 5 days were safe and well tolerated. Pharmacokinetics of Compound A on Day 5 of dosing is similar to that observed on Day 1, suggesting no accumulation in plasma with repeated administration. Oral administration of increasing Compound A doses results in dose-proportional linear pharmacokinetics and Tmax occurs around 1 h after Compound A administration. Pregnant or nursing women are excluded and men and women of childbearing potential use birth control. Compound A does not produce hyperprolactinemia and there are no reports of sexual dysfunction.

Considerations in Drug Prescribing/Drug Drug Interactions:

Compound A is metabolized predominantly by cytochrome P450 3A4 (CYP3A4). It is not a potent inhibitor of any CYP enzyme. Subjects are informed to avoid the use of strong CYP450 inhibitors (e.g macrolide antibiotics, verapamil, aprepitant, grapefruit juice) and strong CYP450 inducers (e.g. phenytoin, carbamazepine oxcarbazepine, phenobarbital, modafinil, rifampicin, Saint John's Wort) during study. SSRIs may elevate the concentration of concomitantly administered Compound A due to the common CYP450 metabolic pathway (paroxetine>fluoxetine>sertraline>citalopram); thus, conservative introduction of Compound A and careful safety monitoring is conducted.

The common side effects risks of SSRI antidepressants are well described elsewhere and are included in the informed consent. One rare potentially serious adverse event is a serotonin syndrome. This syndrome typically occurs within 24 hours of initiation, overdose, or change in dose. Symptoms include: nausea, diarrhea, autonomic instability, elevated temperature, changes in blood pressure, twitching and increased muscle tone, tremor, hyperreflexia, and confusion. To minimize the risk of serotonin syndrome, the investigators provide education to study staff and participants to aid in early recognition and treatment of this syndrome. Other serotonergically active medications (i.e., triptans) are not used during the study. Experienced study physicians, familiar with serotonin syndrome, are available 24 hr/d, 7 d/wk in the event of emergency.

Minimizing Drop-Out:

In order to minimize drop-out, the investigators provide thorough pre-enrollment education for all prospective subjects and confirm the subjects' commitment to and feasibility for follow-up. The investigators also provide ongoing education during the study to reinforce the subjects' commitment. The subject receives a modest payment for participation at each visit to offset the inconvenience of the follow-up appointments and transportation cost. A one-item scale called "Intent-to-Attend" is administered at each study visit. If a subject expresses low intent (i.e., <5), the assessor queries as to the reasons for low intent and attempts to accommodate that subject's needs (e.g., more convenient time of day for appointment) to decrease the chance of losing the subject during follow-up. Also, the clinical research coordinator conducts the study visit in the subject's community if needed.

End of Study:

At the end of study (week 12 or premature exit), all week 12 procedures and assessments are conducted and the subject is started on the most appropriate treatment in the most appropriate setting and referred to his/her previous or newly assigned long-term provider for follow-up. A post-study visit with the research team is scheduled as a routine clinic visit to ensure that the subject has made or scheduled the appropriate follow-up appointments and to address any clinical problems that may have occurred related to previous study procedures, study medication, or any new medication that may have been started at study exit.

D. Data Management and Statistical Plan

Sample Size:

The sample size is based on the pragmatics of recruitment based on experience of ability to screen 2-3 subjects/month per site. During an 8 month enrollment period, approximately 3 subjects per month are enrolled in order to start at least 20 subjects on study mediation. Unless stated otherwise below, analyses adhere to the intention to treat (ITT) principle by including all subjects who take at least one dose of the study medication and return for a least one post-baseline assessment visit.

Preliminary Descriptive Analyses:

The clinical and demographic characteristics of the sample at baseline are examined. Frequency distributions are calculated for all variables. The mean, median, standard deviation, minimum and maximum are calculated on each continuous measure. Categorical variables are presented as frequencies and proportions. Graphical displays including histograms and box plots are produced. These analyses examine baseline CAPS score, gender, age, presence/absence of MDD, disability status, length of illness, and number of past failed adequate medication treatments and all post baseline assessments.

Evaluation of Effects of Compound A in a PTSD Sample:

medians and mean±and standard deviation (sd) of the CAPS (primary outcome), QIDS-SR, CGI-I, PANSS, and SDS by treatment group are determined over time. There is a significant decline in rating scale scores from baseline to the end of the 12-week Compound A treatment period. In addition to change scores, rates of response (≥30% decrease in CAPS) and remission (≥45 on CAPS) are determined Within-group effect sizes using Cohen's d for the continuous outcomes is determined. The number needed to treat (NNT) for response and remission rates is determined. The effect size is a descriptive, not inferential, measure of change; i.e. no significance tests are directly associated with it. The effect size conveys a description of magnitude of change that is independent of sample size. A 95% confidence interval accompanies each effect size to guide their interpretation. In addition, analyses for each outcome variable consist of paired t-tests.

Evaluation of Tolerability, Safety and Side Effects of Compound A in a PTSD Sample:

The safety analyses includes all subjects who have taken at least one dose of study medication and have at least one post-baseline safety evaluation. These analyses include those subjects who have reported an adverse event as well as those who do not report an adverse event. The incidence of treatment emergent adverse events, type of adverse events, and frequency of withdrawals due to an adverse event are summarized. Tolerability by the rate of study medication discontinuation due to medication side effect is evaluated. Pre-post change on the FIBSER, AIMS, SAS, BAS, and SSTS are also evaluated and presented descriptively mean, medians, sd, 95% CI.

Feasibility of Recruitment and Retention:

The reason(s) for prospective participants to decline the study are maintained in the database with a link to an assigned number (i.e. no personal identifiers). In addition, the reason(s) for the prospective subjects to agree to participate in the study, he/she is asked to give a reason(s) for their decision and these reason(s) are also maintained in the database with a link to the assigned number as well as linked to the subject's assigned study number that is given after he/she signs informed consent. All reasons for screen failure and reasons for drop-out prior to starting study medication also are maintained. All reasons for early exit from the treatment study are collected, including side effect, lost to follow-up, non adherence to study protocol, etc. Rates (and 95% CIs) for starting medication and study completion are calculated: 1) the number of subjects approached is divided by the number of subjects enrolled in the study and 2) the number of subjects completed is divided by the number who were started on medication.

Feasibility of the Assessment Process and Data Collection:

The rates of scale completion are calculated for each of the assessments over the course of the study. The database is tested and examined for frequency of missing data.

Subject Acceptance and Satisfaction with the Study Medication:

The Treatment Satisfaction Questionnaire for Medication (TSQM) is completed by each subject at study visits. The means (and 95% CI), medians, and sd is calculated.

Missing Data:

Every effort is made to prevent attrition, e.g., telephone reminders prior to visits, participation fees, meeting with subject in community if needed, reinforcing adherence at each visit, being available to subject if change in appointment time is needed. However, some attrition is inevitable. The analyses will includes all available observations (i.e. from the various assessment times) from each subject. No imputation processes is used to replace missing data. Analyses examine the Intent-to-Attend variable by treatment group over time. At baseline subjects rate their Intent to complete the trial. The ratings are used in two ways. First, effect size estimates of the treatment effect (described above) also are calculated separately for those who provide higher vs. low rating of baseline Intent to Attend (5+ vs. <5). Second, in an effort to reduce risk of attrition, the clinical research coordinator attempts to accommodate the needs of the subject who reports low self-rated Intent, (e.g., changing time of day for next assessment).

Month 1: Study start-up training, procure study medication and supplies, and conduct inservices to initiate enrollment. Enroll first subject. Start data entry.

Month 2-8: Continue enrollment of approximately 3 subjects per month to start 20 subjects on study medication. Meet 50% enrollment (n=10) by end of month 4 and 100% enrollment (n=20) by end of month 8. Data entry is completed within 48 hours of collection.

Month 9-11: All final enrolled subjects complete follow-up assessments. Enrollment closes at month 9. All data are entered and checked.

Month 12: Analysis and final report.

Results:

This single-site, prospective, open label trial study of Compound A as adjunctive treatment to an inadequate response to an SSRI shows that Compound A is effective for the treatment for PTSD. The combination of an SSRI and Compound A offers a complementary mechanism of action that is better than either drug alone.

Example 2: The Effect of Compound A on Reversal of Social Isolation Resulted from Repeated Stress Mice are tested for social isolation behavior after repeated exposure (once daily for 10 days) to an aggressive resident intruder mouse in the social defeat/resident intruder paradigm as describe by Berton et al., *Science* (2006) 311:864-868, the contents of which are incorporated by reference. Mice are then dosed chronically, once daily for 30 d, with either vehicle (5% DMSO/5% Tween-20/15% PEG400/75% water, 6.7 ml/kg volume) or Compound A (1 mg/kg, ip) in vehicle solution. On the day after the last drug or vehicle treatment, the mice are placed in the open field in the presence of a resident intruder mouse and the animal's behavior recorded by videotape for 10 min. The videotapes are then scored for the total time each mouse spent during a 10 min period in specified open-field quadrants. The total time (sec) spent by mice representing each drug treatment group in the Interaction Zone in proximity to the resident intruder mouse or, in the Corner Zones, at a distance from the intruder mouse is expressed as a mean (±SEM).

Results:

Decreased social function is a core feature of the 'negative' symptoms of schizophrenia that are poorly addressed by existing antipsychotic medications. The social defeat/resident intruder model can be used to measure social isolation behavior in rodents. Isolation behavior has been shown to be reversed using this model, after chronic administration of anti-depressant medications with potent SERT activity, including fluoxetine (Berton et al., *Science* (2006) 311:864-868). Neither acute administration of anti-depressant medications or chronic treatment with anti-anxiety medications, like chlordiazepoxide, are similarly effective in this paradigm (Berton et. al., *Science* (2006) 311:864-868). Thus, the model has been proposed for the identification of compounds to address social isolation behavior, such as social isolation behavior resulted from repeated stress. This assay is therefore used to demonstrate reversal of social isolation behavior.

In the experiment described or similarly described above, mice are subjected to exposure to an aggressive resident intruder mouse in the social defeat/resident intruder paradigm as described in Berton et al., *Science* (2006) 311:864-868. They are then dosed chronically, once daily for 30 d, with either vehicle or Compound A (1 mg/kg, IP) in vehicle. On the day after the last drug or vehicle treatment the mice are placed in the open field in the presence of a resident intruder mouse and the total time each mouse spent during a 10 min period in defined open-field quadrants in close proximity to the intruder or in isolation to the intruder is measured. As anticipated, exposure to the aggressor mouse significantly reduced the amount of time resident mice spent in proximity to the intruder ($p<0.05$ compared with vehicle). However, mice treated with Compound A following exposure to the intruder paradigm, showed no significant reduction in time spent in proximity to the intruder (NS, compared with Compound A alone). Compound A treatment alone did not result in differences in time spent in the Interaction Zone, compared with untreated control mice. The data indicate that chronic treatment with Compound A results in a reversal of social defeat behavior comparable to that seen after chronic treatment with anti-depressant medications such as fluoxetine. This experiment shows that Compound A is effective in reversing social isolation resulted from repeated stress. This experiment also shows that Compound A has functional anti-depressant activity.

The invention claimed is:

1. A method for the treatment of posttraumatic stress disorder, comprising administering to a patient in need thereof an effective amount of a compound of Formula I:

Formula I

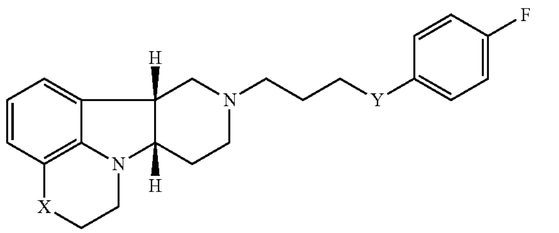

wherein X is O, —NH or —N($CH_3$); and Y is —O—, —C(H)(OH)—or —C(O)—, in free or pharmaceutically acceptable salt form.

2. The method according to claim 1, wherein the compound of Formula I is selected from a group consisting of compounds of formula I wherein:

X is —O— and Y is —C(H)(OH)—,
X is —NH— and Y is —C(H)(OH)—,
X is —N($CH_3$)— and Y is —C(H)(OH)—,
X is —O— and Y is —C(O)—,
X is —O— and Y is —O—,
X is —N($CH_3$)— and Y is —C(O)—,
X is —N($CH_3$)— and Y is —O—,
X is —NH— and Y is —C(O)—, and
X is —NH— and Y is —O—.

3. The method of claim 1, wherein X is —N($CH_3$)— and Y is —C(O)—.

4. The method of claim 1, wherein the administration of the compound of Formula I is an adjunct to the administration of one or more additional antidepressants.

5. The method of claim 4, wherein the administration of one of more additional antidepressants is an adjunct to administration of the compound of Formula I.

6. The method of claim 4, wherein the antidepressant is selected from one or more of amitriptyline, amoxapine, bupropion, citalopram, clomipramine, desipramine, doxepin, duloxetine, escitalopram, fluoxetine, fluvoxamine, imipramine, isocarboxazid, maprotiline, mirtazapine, nefazodone, nortriptyline, paroxetine, phenelzine sulfate, protriptyline, sertraline, tranylcypromine, trazodone, trimipramine, and venlafaxine, in free or pharmaceutically acceptable salt form.

7. The method of claim 4, wherein the antidepressant is one or more antidepressants selected from selective serotonin reuptake inhibitors (SSRIs), serotonin-norepinephrine reuptake inhibitors (SNRIs), and tricyclic antidepressants.

8. The method of claim 7, wherein the antidepressant is a SSRI.

9. The method of claim 1, wherein the compound of Formula I is administered orally as a composition comprising a pharmaceutically acceptable diluent or carrier as an oral unit dose form that is a tablet or capsule.

10. The method of claim 1, wherein the effective amount of the compound of Formula I is a daily dose of about 10 mg to about 50 mg.

11. The method of claim 1, wherein the effective amount of the compound of Formula I is a daily dose of about 20 mg to about 40 mg.

12. The method of claim 1, wherein the effective amount of the compound of Formula I is a daily dose of about 1 mg to about 10 mg.

13. The method of claim 1, further comprising administering one or more additional therapeutic agents selected from compounds that modulate GABA activity, a 5-HT modulator, a melatonin agonist, an ion channel modulator, a serotonin-2 antagonist/reuptake inhibitor, an orexin receptor antagonist, an H3 agonist, a noradrenergic antagonist, a galanin agonist, a CRH antagonist, human growth hormone, a growth hormone agonist, estrogen, an estrogen agonist, a neurokinin-1 drug, and an antipsychotic agent, in free or pharmaceutically acceptable salt form.

14. The method of claim 1, further comprising administering one or more additional therapeutic agents selected from a group consisting of modafinil, armodafinil, doxepin, alprazolam, bromazepam, clobazam, clonazepam, clorazepate, diazepam, flunitrazepam, flurazepam, lorazepam, midazolam, nitrazepam, oxazepam, temazepam, triazolam, indiplon, zopiclone, eszopiclone, zaleplon, Zolpidem, gaboxadol, vigabatrin, tiagabine, estazolam, ketanserin, risperidone, eplivanserin, volinanserin, pruvanserin, repinotan, sarizotan, eptapirone, buspirone, melatonin, ramelteon agomelatine, lamotrigine, gabapentin, pregabalin, orexin, ritanserin, nefazodone, serzone, trazodone, Casopitant, amitriptyline, amoxapine, bupropion, citalopram, clomipramine, desipramine, doxepin, duloxetine, escitalopram, fluoxetine, fluvoxamine, imipramine, isocarboxazid, maprotiline, mirtazapine, nortriptyline, paroxetine, phenelzine sulfate, protriptyline, sertraline, tranylcypromine, trimipramine, venlafaxine, chlorpromazine, haloperidol, droperidol, fluphenazine, loxapine, mesoridazine molindone, perphenazine, pimozide, prochlorperazine, promazine, thioridazine, thiothixene, trifluoperazine, clozapine, aripiprazole, olanzapine, quetiapine, risperidone, ziprasidone, and paliperidone, in free or pharmaceutically acceptable salt form.

15. The method of claim 1, wherein the patient has not responded adequately to treatment with another antidepressant or combination of antidepressants.

16. The method of claim 14, wherein the patient has not responded to treatment with one or more antidepressants selected from selective serotonin reuptake inhibitors (SSRIs), serotonin-norepinephrine reuptake inhibitors (SNRIs), and tricyclic antidepressants.

17. The method of claim 16, wherein the patient has not responded to treatment with a SSRI.

18. The method of claim 16, wherein the selective serotonin reuptake inhibitors are selected from the group consisting of citalopram, escitalopram oxalate, fluoxetine, fluvoxamine maleate, paroxetine, sertraline, and dapoxetine.

19. The method of claim 16, wherein the serotonin-norepinephrine reuptake inhibitors are selected from venlafaxine, desvenlafaxine, duloxetine, milnacipran, levomilnacipran, and sibutramine.

20. The method of claim 17, wherein the selective serotonin reuptake inhibitors are selected from the group consisting of citalopram, fluoxetine, paroxetine, and sertraline.

21. The method of claim 3, wherein the compound of Formula I is in the form of a toluenesulfonic acid salt.

* * * * *